(12) United States Patent
Kii et al.

(10) Patent No.: US 11,941,801 B2
(45) Date of Patent: *Mar. 26, 2024

(54) IMAGING DEVICE, SYSTEM, AND PROGRAM FOR EVALUATING CELL CULTURES

(71) Applicant: NIKON CORPORATION, Tokyo (JP)

(72) Inventors: Hiroaki Kii, Kawasaki (JP); Shinichi Takayama, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 615 days.

This patent is subject to a terminal disclaimer.

(21) Appl. No.: 17/128,865

(22) Filed: Dec. 21, 2020

(65) Prior Publication Data

US 2021/0110542 A1 Apr. 15, 2021

Related U.S. Application Data

(63) Continuation of application No. PCT/JP2018/024663, filed on Jun. 28, 2018.

(51) Int. Cl.
*G06T 7/00* (2017.01)
*C12M 1/34* (2006.01)
(Continued)

(52) U.S. Cl.
CPC ........... *G06T 7/0012* (2013.01); *C12M 41/46* (2013.01); *G01N 15/0227* (2013.01); *G01N 33/4833* (2013.01); *G06T 7/60* (2013.01); *G06T 7/70* (2017.01); *G01N 2015/0065* (2013.01); *G06T 2207/20092* (2013.01); *G06T 2207/30024* (2013.01)

(58) Field of Classification Search
None
See application file for complete search history.

(56) References Cited

U.S. PATENT DOCUMENTS

2012/0106822 A1* 5/2012 Mimura ................. C12M 41/48
382/133
2016/0335767 A1* 11/2016 Matsumoto .......... G06V 20/695
(Continued)

FOREIGN PATENT DOCUMENTS

JP S63-113358 A 5/1988
JP 2015-130806 A 7/2015
(Continued)

OTHER PUBLICATIONS

Office Action corresponding to Japanese Application No. 2020-526817, dated Jun. 7, 2022 with English Translation.
(Continued)

*Primary Examiner* — Soo Shin
(74) *Attorney, Agent, or Firm* — FOLEY & LARDNER LLP

(57) ABSTRACT

A device includes: a distribution information acquiring part configured to acquire, based on an image in which a plurality of cells that are cultivated in a predetermined area are imaged, distribution information relating to a distribution in the predetermined area of the plurality of cells; and a determination part configured to determine a cultivated state of the plurality of cells based on the distribution information acquired by the distribution information acquiring part.

11 Claims, 21 Drawing Sheets

(51) Int. Cl.
  *G01N 15/00*   (2006.01)
  *G01N 15/02*   (2006.01)
  *G01N 33/483*  (2006.01)
  *G06T 7/60*    (2017.01)
  *G06T 7/70*    (2017.01)

(56) References Cited

U.S. PATENT DOCUMENTS

2017/0089820 A1* 3/2017 Wong .................... C12M 41/48
2017/0159004 A1* 6/2017 Senda ................... C12M 41/36
2021/0125335 A1* 4/2021 Kii ........................ G06V 10/56
2022/0114819 A1* 4/2022 Ichihashi ............... G06T 7/246

FOREIGN PATENT DOCUMENTS

JP   2015-170047 A   9/2015
JP   2016-021915 A   2/2016

OTHER PUBLICATIONS

Office Action issued in corresponding British Patent Application No. 2020538.1, dated Feb. 1, 2023 (4 pages).
International Search Report issued in corresponding application No. PCT/JP2018/024663 dated Oct. 2, 2018 with English translation.
Written Opinion issued in corresponding application No. PCT/JP2018/024663 dated Oct. 2, 2018 with English translation.

* cited by examiner

IMAGING DEVICE, SYSTEM, AND PROGRAM FOR EVALUATING CELL CULTURES

CROSS-REFERENCE TO RELATED APPLICATION

This is a Continuation Application of International Application No. PCT/JP2018/024663, filed on Jun. 28, 2018. The contents of the aforementioned applications are incorporated herein by reference.

BACKGROUND

Field of the Invention

The present invention relates to a device, a system, and a program.

Background

Generally, for the purpose of regenerative medicine, technologies for evaluating the degree of maturity of epithelial cells such as RPE cells and epidermal cells have become a generic technology in a broad field including advanced medical fields such as regenerative medicine and screening of pharmaceuticals. In the process of evaluating the degree of maturity of cells, it is required to accurately determine whether the cells are immature or over-mature, in other words, to accurately determine the state of the cells. As one example, a keratin testing method for testing the state of skin keratinocytes by clarifying the state of the skin keratinocytes by collecting the skin keratinocytes using a tape stripping method and dying the skin keratinocytes has been disclosed (see Japanese Unexamined Patent Application, First Publication No. S63-113358).

SUMMARY

In order to solve the problem described above, according to one embodiment of the present invention, there is provided a device including: a distribution information acquiring part configured to acquire, based on an image in which a plurality of cultivated cells are imaged, distribution information relating to a distribution in a predetermined area of the plurality of cells; and a determination part configured to determine a cultivated state of the plurality of cells based on the distribution information acquired by the distribution information acquiring part.

Further, according to one embodiment of the present invention, there is provided a determination system including: the device described above; and an imaging part configured to generate the image by imaging a target object.

Further, according to one embodiment of the present invention, there is provided a program causing a computer to execute: a distribution information acquiring step of acquiring, based on an image in which a plurality of cells that are cultivated in a predetermined area are imaged, distribution information relating to a distribution in the predetermined area of the plurality of cells; and a determination step of determining a cultivated state of the plurality of cells based on the distribution information acquired in the distribution information acquiring step.

DESCRIPTION OF EMBODIMENTS

[Regarding Characteristics of Maturation of Cell]
First, characteristics of maturation of cells will be described.

In other to evaluate a cultured state of cells, it is required to accurately determine the maturity thereof. More specifically, in a case in which epithelial cells such as RPE cells and epidermal cells are cultivated for the purpose of regenerative medicine, in order to generate cells for transplantation, cell sheets, and the like by cultivating such epithelial cells, generally, the epithelial cells are cultivated until the cells become appropriately mature. When such epithelial cells become appropriately mature, a plurality of cells become a honeycomb shape. A determination system according to an embodiment determines the state of cells using features of maturation of the cells.

First Embodiment

Figure 1:
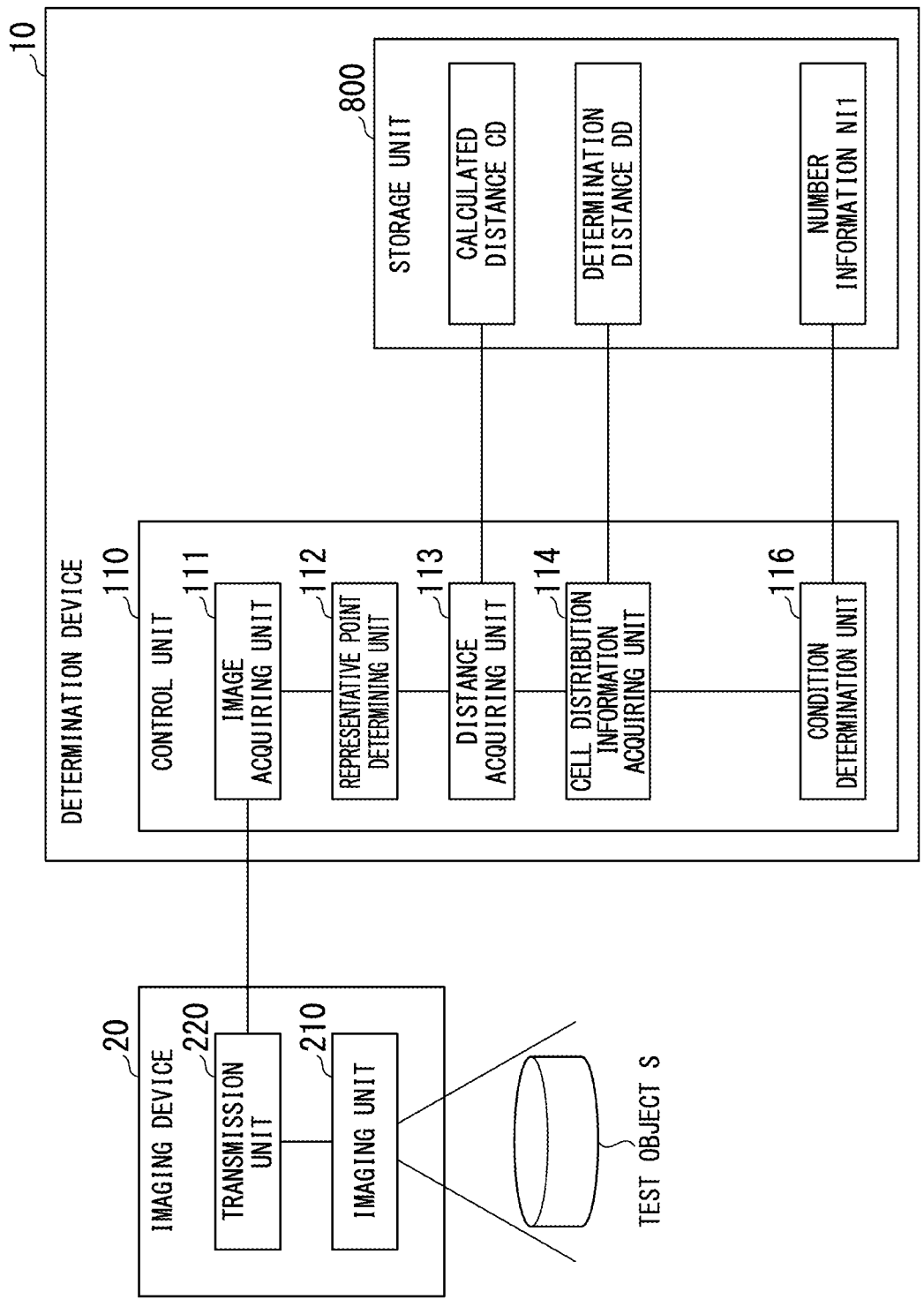
FIG. 1 is a diagram illustrating an example of the configuration of a determination system 1 according to a first embodiment.

Hereinafter, a first embodiment of the present invention will be described with reference to the drawings. FIG. 1 is a diagram illustrating an example of the configuration of a determination system 1 according to a first embodiment. The determination system 1 includes a determination device 10 and an imaging device 20.

The imaging device 20 includes an imaging unit 210 and a transmission unit 220. The imaging unit 210 images a test object S that is a target object for imaging. The test object S, for example, is a plurality of cells cultivated in a Petri dish or the like. The transmission unit 220 transmits a captured image CI that is an image of the test object S imaged by the imaging unit 210 to the determination device 10.

Figure 2:
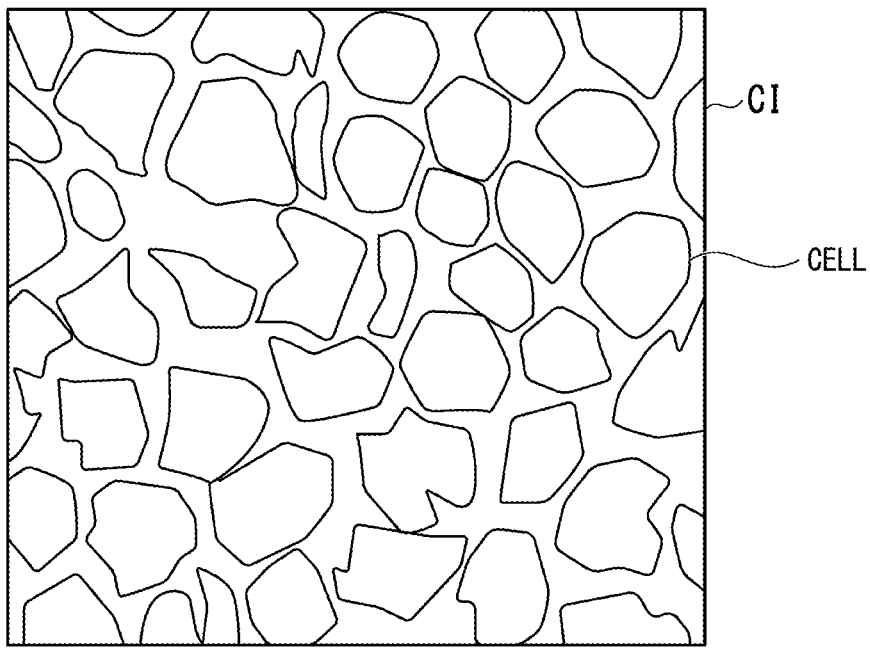
FIG. 2 is a diagram illustrating an example of a captured image CI according to the first embodiment.

Here, a specific example of the captured image CI will be described. FIG. 2 is a diagram illustrating an example of the captured image CI according to the first embodiment. As illustrated in FIG. 2, the captured image CI is an image that represents part of the test object S imaged by the imaging unit 210. In other words, an image of cells present in part of the test object S imaged by the imaging unit 210 is included in the captured image CI.

Referring back to FIG. 1, the determination device 10 will be described. The determination device 10 includes a control unit 110 and a storage unit 800. For example, the control unit 110 realizes an image acquiring unit 111, a representative point determining unit 112, a distance acquiring unit 113, a cell distribution information acquiring unit 114, and a condition determination unit 116 as its functional units by using a processor such as a central processing unit (CPU) executing a program (software). Some or all of such constituent elements may be realized by hardware (a circuit unit; including circuitry) such as a large scale integration (LSI), an application specific integrated circuit (ASIC), a field-programmable gate array (FPGA), or a graphics processing unit (GPU) or may be realized by software and hardware in cooperation. The program may be stored in the storage unit 800 in advance or may be stored in an attachable/detachable storage medium such as a DVD or a CD-ROM and be installed in the storage unit 800 by loading the storage medium into a drive device.

The storage unit 800, for example, is realized by an HDD, a flash memory, an electrically erasable programmable read only memory (EEPROM), a read only memory (ROM), a random access memory (RAM), or the like. For example, programs that are read and executed by a processor are stored in the storage unit 800. In addition, information representing a calculated distance CD, information representing a determination distance DD, and number information NI1 are stored in the storage unit 800. Details of the information will be described below.

The image acquiring unit 111 acquires a captured image CI from the imaging unit 210. The image acquiring unit 111 supplies this captured image CI to the representative point determining unit 112. The representative point determining unit 112 determines representative points P of a plurality of cells included in the captured image CI acquired from the image acquiring unit 111 for each of the cells. For example, the representative point P is a point that represents a center of a cell for each cell.

Figure 3:
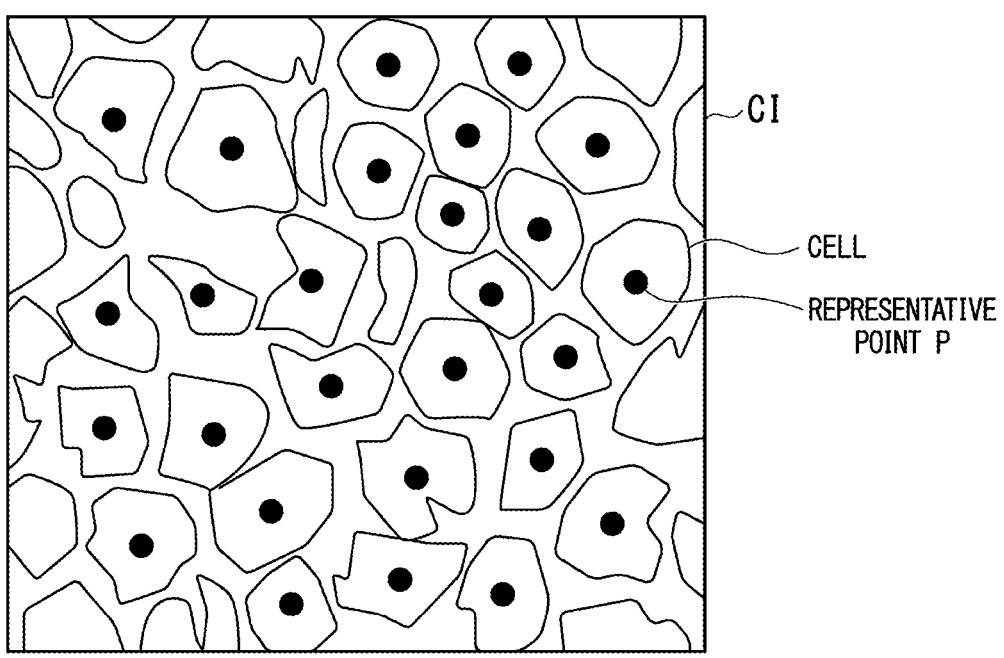
FIG. 3 is a diagram conceptually illustrating the process of a representative point determining unit 112 according to this first embodiment.

Here, a specific example of the process of the representative point determining unit 112 will be described. FIG. 3 is a diagram conceptually illustrating the process of the representative point determining unit 112 according to this first embodiment. The representative point determining unit 112 executes a peak detection process on the acquired captured image CI and determines representative points P for a plurality of cells included in the captured image CI. The representative point determining unit 112 supplies information representing representative points P of a plurality of cells appearing in the captured image CI to the distance acquiring unit 113. The representative point determining unit 112, for example, supplies identification information (for example, numbers assigned to pixels of the captured image CI) of pixels representing the positions of the representative points P in the captured image CI to the distance acquiring unit 113 as information representing the representative points P.

The distance acquiring unit 113 acquires information representing representative points P of a plurality of cells determined by the representative point determining unit 112. The distance acquiring unit 113 acquires a distance between a certain representative point P and another representative point P included in the captured image CI. More specifically, the distance acquiring unit 113 sets one certain representative point P included in the captured image CI as a reference and calculates an inter-representative point distance d from the representative point P serving as the reference to another representative point P present in a range up to a distance represented by a calculated distance CD. The calculated distance CD is a distance serving as an index when the distance acquiring unit 113 calculates a mutual distance between representative points P and is a distance that may be taken by representative points P in a case in which cells are in the process of maturation from being immature to being over-mature.

Figure 4:
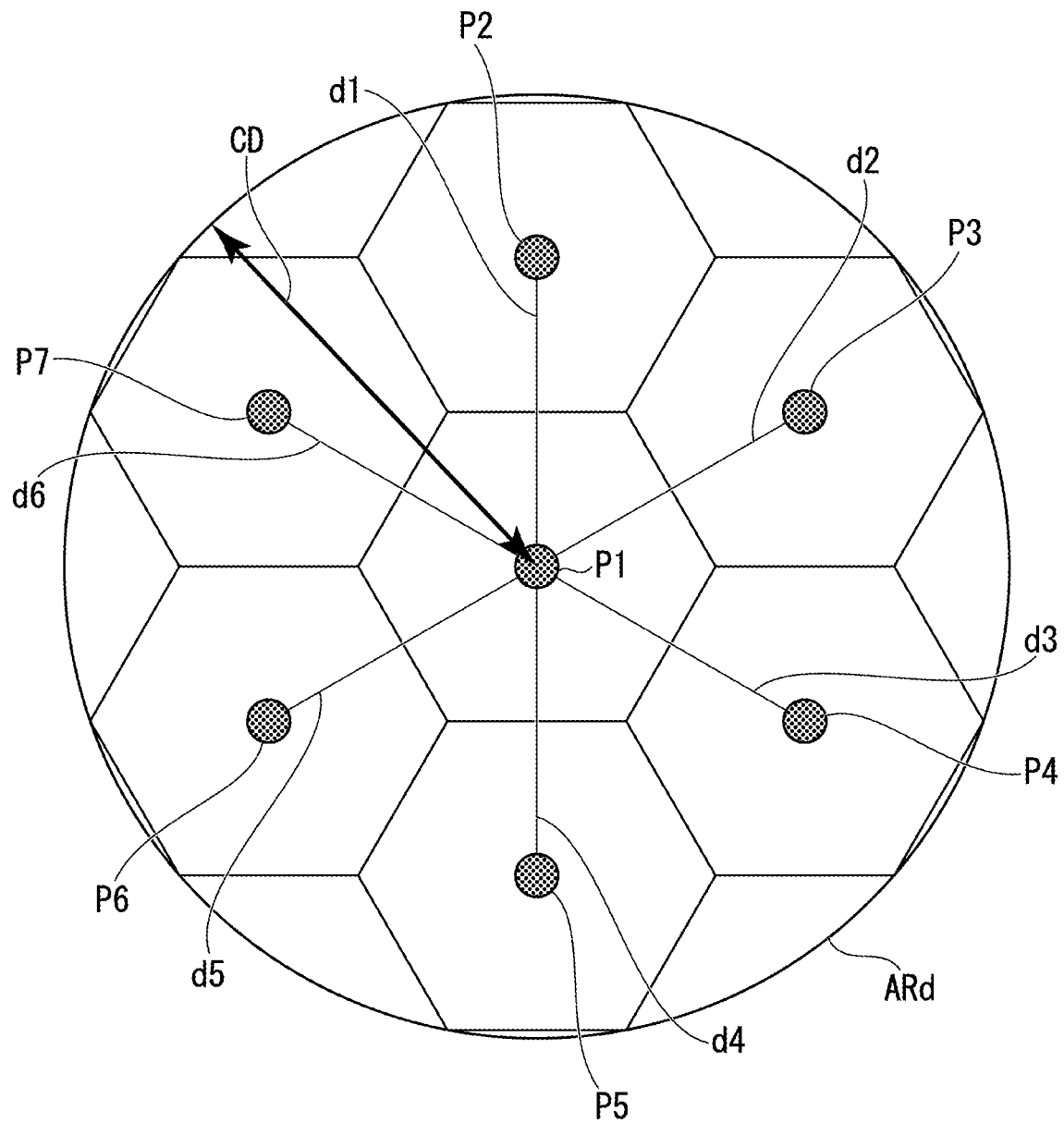
FIG. 4 is a diagram schematically illustrating an example of an inter-representative point distance d according to the first embodiment.

Hereinafter, details of the inter-representative point distance d calculated by the distance acquiring unit 113 will be described with reference to FIG. 4. FIG. 4 is a diagram schematically illustrating an example of the inter-representative point distanced according to the first embodiment. In the example illustrated in FIG. 4, a case in which a representative point P serving as a reference among representative points P included in a captured image CI is a representative point P1 will be described. First, the distance acquiring unit 113 selects (extracts) representative points P that are present in a target range ARd from the representative point P1 to a distance represented by the calculated distance CD in the captured image CI. Next, the distance acquiring unit 113 acquires inter-representative point distances d (inter-representative point distances d1 to d6 illustrated in the drawing) to representative points P other than the representative point P1 (representative points P2 to P7 illustrated in the drawing) present within the target range ARd. The distance acquiring unit 113, for example, performs a similar process with each one of all the representative points P included in the captured image CI being set as the representative point P1. Thus, the distance acquiring unit 113 acquires information representing the inter-representative point distances d1 to d6 with each of the representative points P of cells imaged in the captured image CI being set as the representative point P1 for each representative point P and supplies the acquired information to the cell distribution information acquiring unit 114.

The cell distribution information acquiring unit 114 generates cell distribution information DI1 on the basis of the inter-representative point distances d acquired by the distance acquiring unit 113 and a determination distance DD. The determination distance DD is an inter-representative point distance d in a case in which it is determined that cells are appropriately mature. The cell distribution information DI1 is information in which the number of inter-representative point distances d that are equal to or less than the determination distance DD among the inter-representative point distances d1 to d6 and a frequency (the number of reference representative points or the number of reference cells) are associated with each other.

Figure 5:
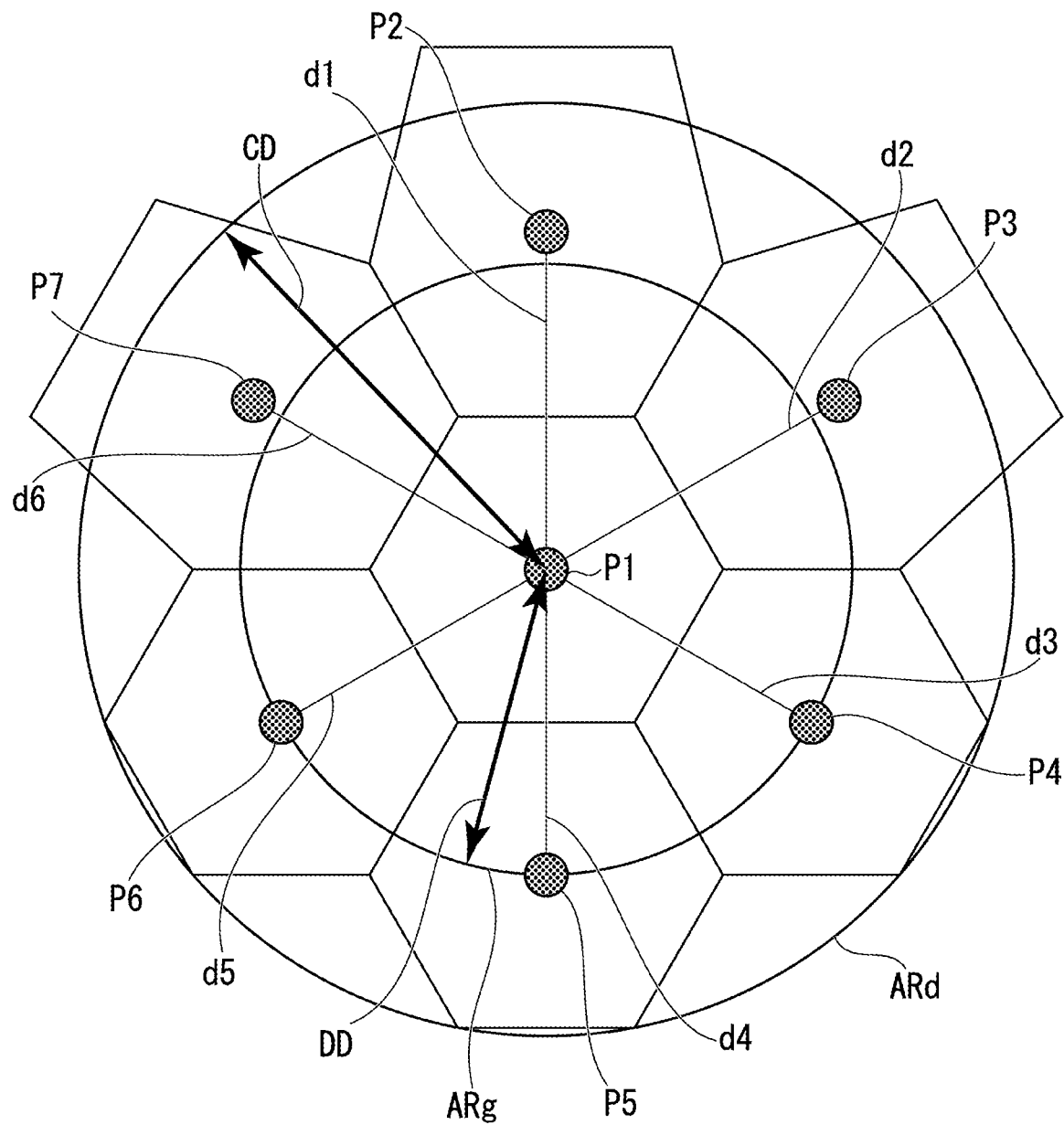
FIG. 5 is a diagram schematically illustrating the process of a cell distribution information acquiring unit 114 according to the first embodiment.

Hereinafter, details of the process of the cell distribution information acquiring unit 114 will be described with reference to FIG. 5. FIG. 5 is a diagram schematically illustrating the process of the cell distribution information acquiring unit 114 according to the first embodiment. In the example illustrated in FIG. 5, a case in which a representative point P serving as a reference is a representative point P1 will be described. In the example illustrated in FIG. 5, representative points P that are present in a target range ARd from the representative point P1 (representative points P2 to P7 illustrated in the drawing) and are present in a determination range ARg to a distance represented by the determination distance DD are three representative points P4 to P6. The cell distribution information acquiring unit 114 calculates the number of different representative points P that are present within the target range ARd having a representative point P as its center for each of representative points P of cells imaged in a captured image CI and have inter-representative point distances d equal to or less than the determination distance DD and generates cell distribution information DI1 in which the numbers and frequencies of the numbers are associated with each other. The cell distribution information acquiring unit 114 supplies the generated cell distribution information DI1 to the condition determination unit 116. The number of representative points P of different target objects present in the target range ARd having a representative point P of a certain cell as its center among a plurality of cells is an example of "characteristics of a target object".

Figure 6:
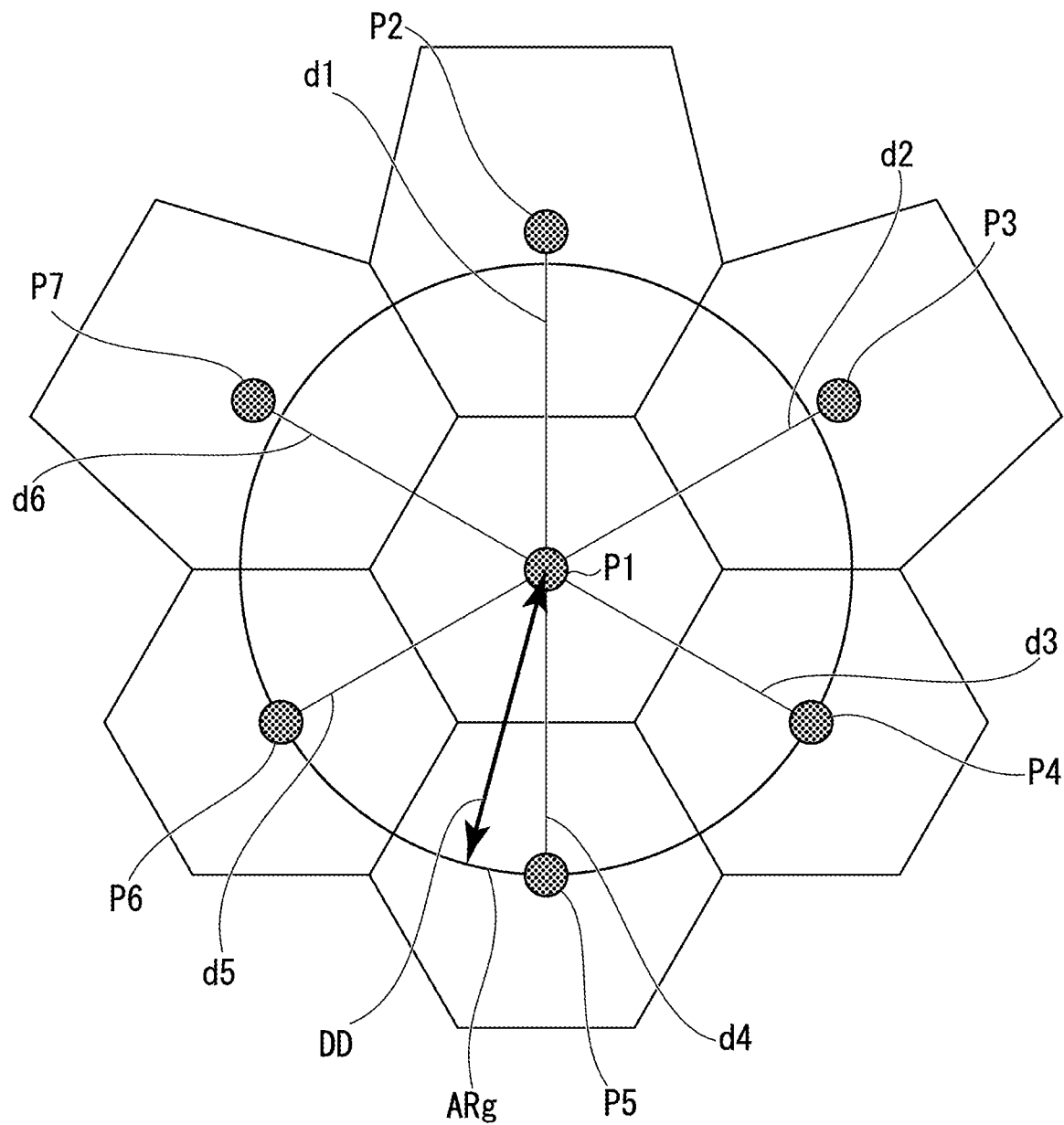
FIG. 6 is a diagram schematically illustrating another example of the process of the cell distribution information acquiring unit 114 according to the first embodiment.

In the description presented above, the cell distribution information acquiring unit 114 may not perform the process of determining representative points P that are present in the target range ARd from the representative point P1. FIG. 6 is a diagram schematically illustrating another example of the process of the cell distribution information acquiring unit 114 according to the first embodiment. In this case, the cell distribution information acquiring unit 114 may calculate the number of representative points d having inter-representative point distances d equal to or less than the determination distance DD with the representative point P set as a center for each of representative points P of cells imaged in the captured image CI and generate cell distribution information DI1 in which the numbers and frequencies of the numbers are associated with other.

Figure 7:
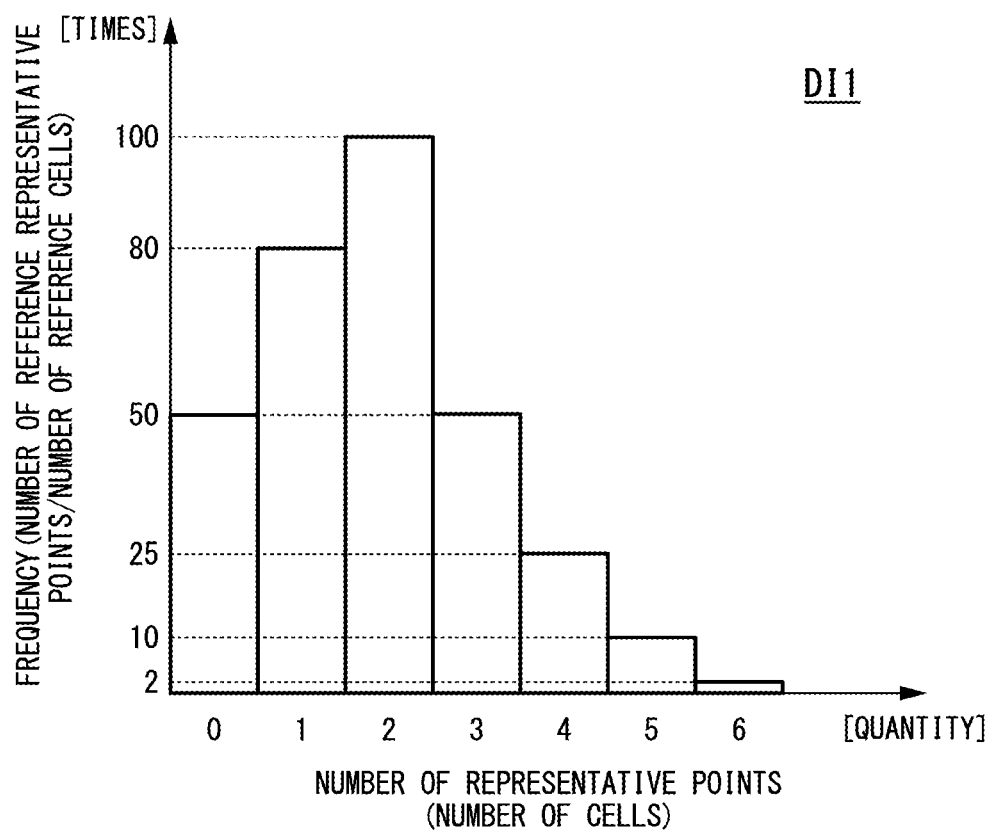
FIG. 7 is a diagram illustrating an example of cell distribution information DI according to the first embodiment.

FIG. 7 is a diagram illustrating an example of the cell distribution information DI1 according to the first embodiment. In the example illustrated in FIG. 7, the cell distribution information acquiring unit 114, for representative points P of 317 cells imaged in a captured image CI, generates cell distribution information DI1 on the basis of the inter-representative point distances d1 to d6 acquired for each representative point P and a determination distance DD. In the example illustrated in FIG. 7, the cell distribution information DI1 represents that a cell of which the number of different representative points P present in the determination range ARg to a distance represented by the determination distance DD is 0 has been detected 50 "times", a cell of which the number of different representative points P present in the determination range ARg to the distance represented by the determination distance DD is 1 has been detected 80 "times", a cell of which the number of different representative points P present in the determination range ARg to the distance represented by the determination distance DD is 2 has been detected 100 "times", a cell of which the number of different representative points P present in the determination range ARg to the distance represented by the determination distance DD is 3 has been detected 50 "times", a cell of which the number of different representative points P present in the determination range ARg to the distance represented by the determination distance DD is 4 has been detected 25 "times", a cell of which the number of different representative points P present in the determination range ARg to the distance represented by the determination distance DD is 5 has been detected 10 "times", and there are two cells of which the number of different representative points P present in the determination range ARg to the distance represented by the determination distance DD is 6.

The condition determination unit 116 determines whether or not the conditions (for example, a degree of maturity) of cells imaged in the captured image CI are good on the basis of the cell distribution information DI1 generated by the cell distribution information acquiring unit 114 and the number information NI1. The number information NI1 is information representing the number of representative points Pother than a representative point P serving as a reference that are present in a range (hereinafter, referred to as a determination range ARg) from the representative point P serving as the reference to a distance represented by a determination distance DD in a case in which cells are assumed to be appropriately mature. Here, in a case in which cells are assumed to be appropriately mature, cells adjacent to each other are arranged in a honeycomb shape. In a case in which cells (representative points P) are arranged in a honeycomb shape, the number information NI1 that may be taken is 6. Thus, in a case in which the number of representative points P present in the determination range ARg coincides with the number information NI1, the cells are determined to be appropriately mature.

The condition determination unit 116 determines that the cells are mature in a case in which the number represented by the number information NI1 coincides with the number having the highest frequency represented by the cell distribution information DI1 and determines that the cells are immature in a case in which the number represented by the number information NI1 does not coincide with the number having the highest frequency represented by the cell distribution information DI1.

In the description presented above, although a case in which the cell distribution information DI1 is information in which the number of inter-representative point distances d equal to or less than the determination distance DD among the inter-representative point distances d1 to d6 and the frequency are associated with each other has been described, the cell distribution information is not limited thereto. The cell distribution information DI1 may be information that represents the number of inter-representative point distances d, which are equal to or less than the determination distance DD, including the representative point P1 serving as the reference.

<Process Flow>

Figure 8:
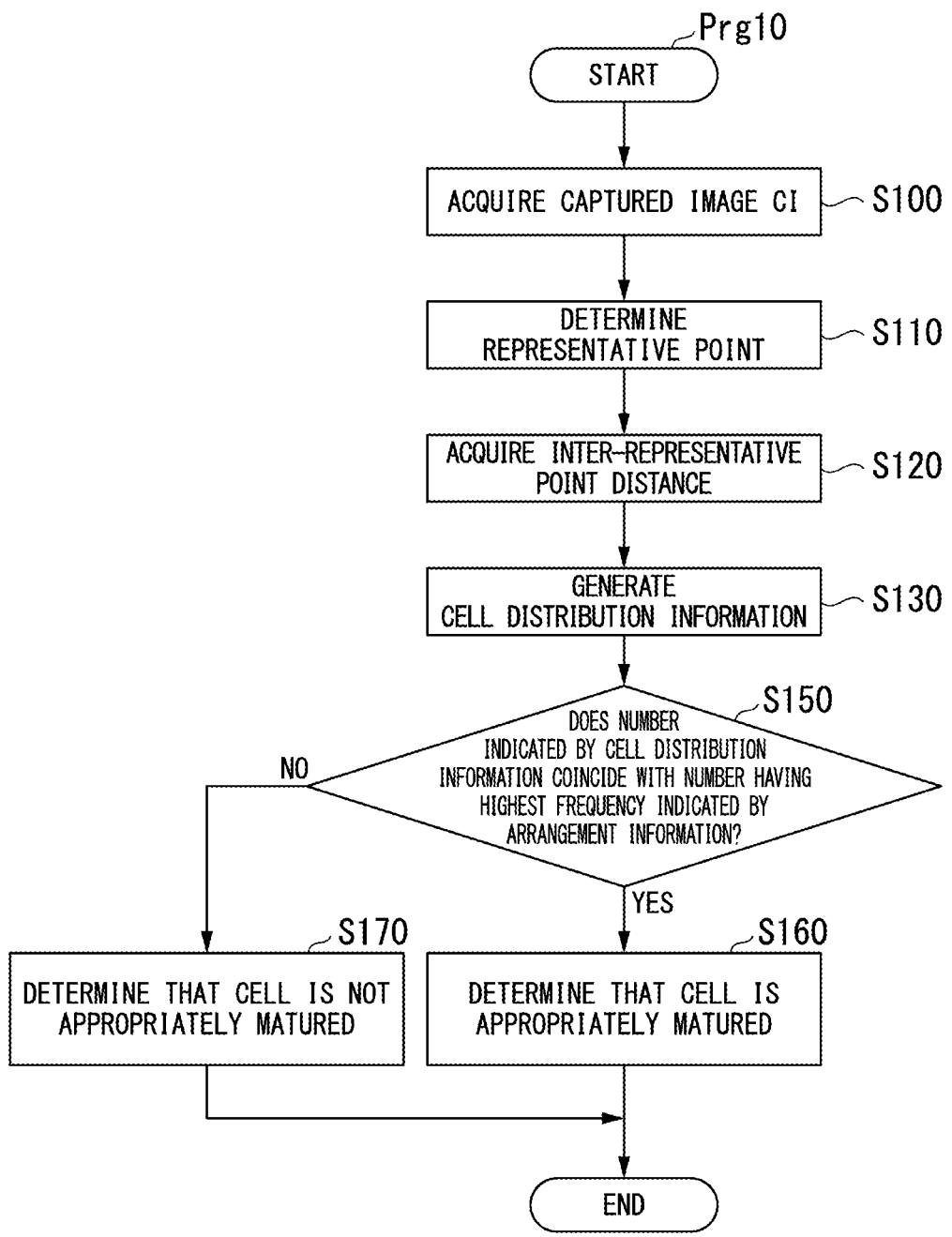
FIG. 8 is a flowchart illustrating an example of the operation of a determination device 10 according to the first embodiment.

Next, an operation of the determination device 10 determining a degree of maturity of cells will be described with reference to FIG. 8. FIG. 8 is a flowchart illustrating an example of the operation of the determination device 10 according to the first embodiment. The determination device 10 executes Steps S100 to S170 illustrated in FIG. 8 on the basis of a determination program Prg10 that is a control program for determining whether or not cells are appropriately mature.

The image acquiring unit 111 acquires a captured image CI from the imaging device 20 and supplies the acquired captured image CI to the representative point determining unit 112 (Step S100). The representative point determining unit 112 determines representative points P of cells imaged in the captured image CI acquired from the image acquiring unit 111 (Step S110). The distance acquiring unit 113 acquires inter-representative point distances d between other representative points P present within a target range ARd from a representative point P serving as a reference among the representative points P determined by the representative point determining unit 112 and the reference representative point P (Step S120). The cell distribution information acquiring unit 114 generates cell distribution information DI1 on the basis of the inter-representative point distances d for each representative point P acquired by the distance acquiring unit 113 (Step S130). The condition determination unit 116 determines that the cells are mature on the basis of the cell distribution information DI1 generated by the cell distribution information acquiring unit 114 and the number information NI1 (Step S150). The condition determination unit 116, for example, determines that the cells imaged in the captured image CI are mature in a case in which the number represented by the number information NI1 coincides with the number, which has the highest frequency, represented by the cell distribution information DI1 (Step S150; Yes) (Step S160). In addition, the condition determination unit 116, for example, determines that the cells imaged in the captured image CI are immature in a case in which the number represented by the number information NI1 does not coincide with the number, which has the highest frequency, represented by the cell distribution information DI1 (Step S150; No) (Step S170).

Summary of First Embodiment

As described above, the determination system 1 according to this embodiment includes the determination device 10 and the imaging device 20, includes a distribution information acquiring unit (in this example, the cell distribution information acquiring unit 114) that acquires distribution information (in this example, the cell distribution information DI1) relating to a distribution in a predetermined area of a plurality of cells on the basis of an image in which a plurality of cultivated cells are imaged (in this example, the captured image CI) and a determination unit (in this example, the condition determination unit 116) that determines a cultivated state of a plurality of cells on the basis of the cell distribution information DI1 acquired by the cell distribution information acquiring unit 114, and determines whether or not the condition (in this example, the degree of maturity) of the cells is good and can improve the accuracy of the determination of the degree of maturity of the cells.

In addition, in the determination system 1 according to this embodiment, a characteristics acquiring unit (in this example, the representative point determining unit 112 and the distance acquiring unit 113) acquires characteristics (in this example, the inter-representative point distance d) of other cells present in a predetermined range (in this example, the target range ARd) from a certain cell among the cells appearing in the captured image CI. In this way, the determination system 1 according to this embodiment can limit cells of which inter-representative point distances d with respect to a certain cell need to be acquired, and thus, the load of the process relating to the determination of the degree of maturity of cells can be reduced.

Second Embodiment

Next, a second embodiment of the present invention will be described. In the first embodiment, a case in which the determination device 10 generates cell distribution information DI on the basis of the inter-representative point distances d and determines a degree of maturity of cells has been described. In the second embodiment, a case in which a determination device 10a determines the degree of maturity of cells on the basis of an angle formed by segments respectively joining a representative point P serving as a reference and other two representative points P will be described. The same reference signs will be assigned to the same components as those according to the embodiment described above, and description thereof will be omitted.

Figure 9:
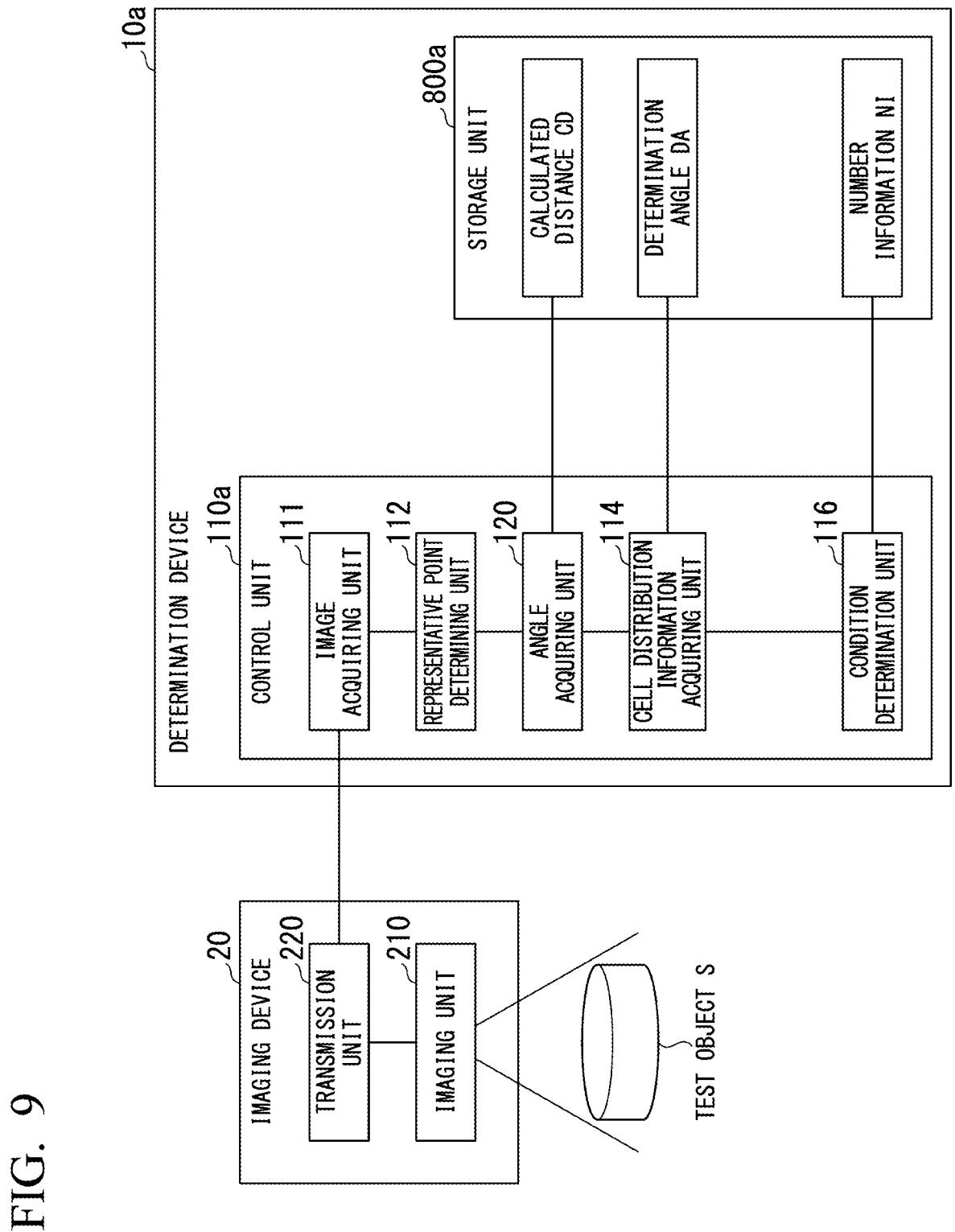
FIG. 9 is a diagram illustrating an example of the configuration of a determination system 2 according to a second embodiment.

Hereinafter, the configuration of a determination system 2 will be described with reference to FIG. 9. FIG. 9 is a diagram illustrating an example of the configuration of the determination system 2 according to the second embodiment. The determination system 2 includes a determination device 10a and an imaging device 20.

The determination device 10a includes a control unit 110a and a storage unit 800a. The control unit 110a, instead of (or in addition to) the components included in the control unit 110, realizes an image acquiring unit 111, a representative point determining unit 112, a cell distribution information acquiring unit 114, a condition determination unit 116, and an angle acquiring unit 120 as its functional units. For example, information representing a calculated distance CD, information representing a determination angle DA, and number information NI1 are stored in the storage unit 800a. Details of the determination angle DA will be described below.

The angle acquiring unit 120 acquires information representing representative points P of a plurality of cells determined by the representative point determining unit 112. The angle acquiring unit 120 sets one certain representative point P included in a captured image CI as a reference and acquires an angle formed by segments respectively joining other representative points P, which are present in a range from the representative point P serving as the reference to a distance represented by a calculated distance CD, of two different target objects adjacent to each other around a vertical axis having the representative point P serving as the reference as its center and a certain representative point P (hereinafter, referred to as a representative point angle ag).

Figure 10:
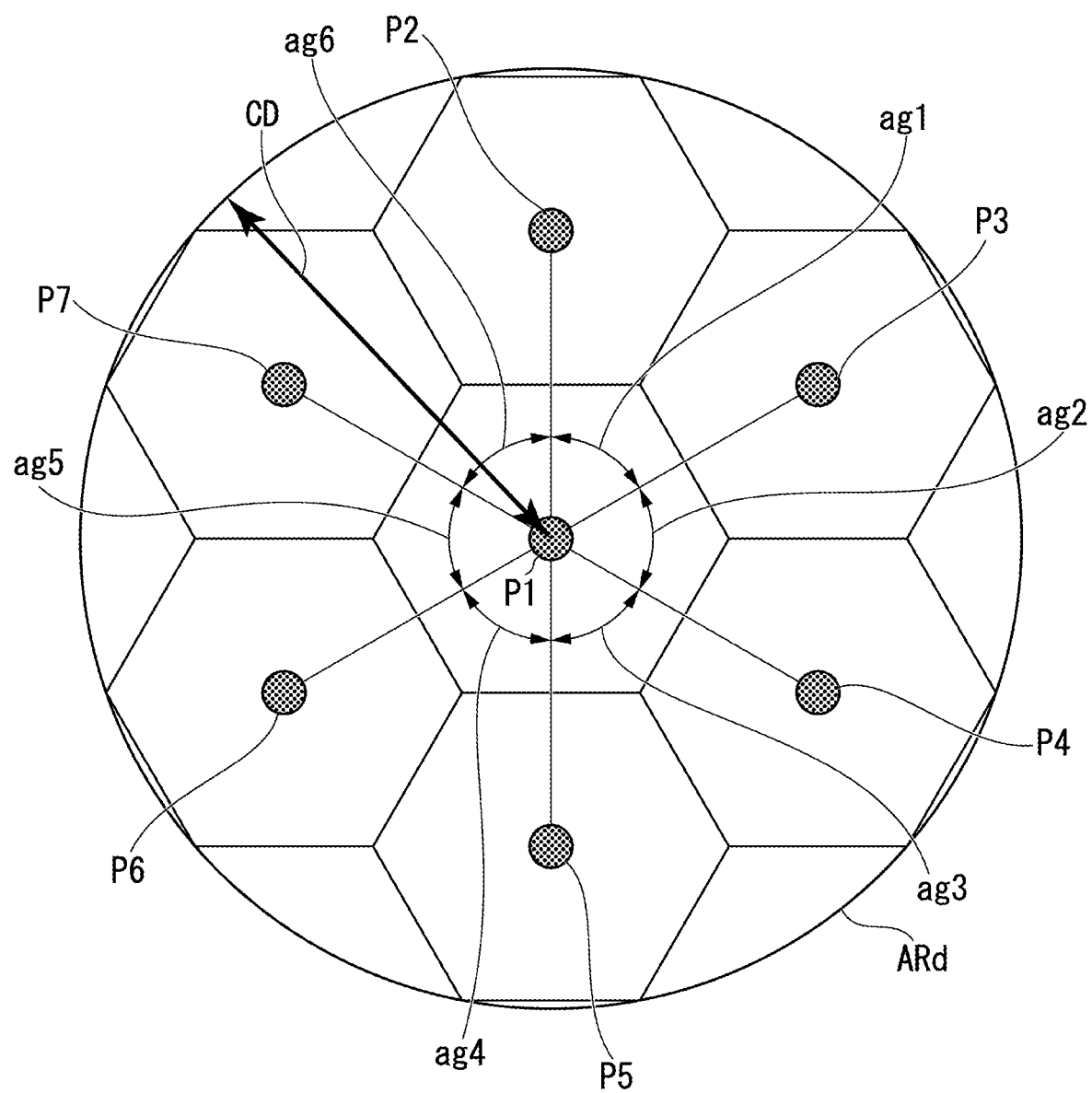
FIG. 10 is a diagram schematically illustrating an example of a representative point angle ag according to the second embodiment.

Hereinafter, details of the representative point angle ag calculated by the angle acquiring unit 120 will be described with reference to FIG. 10. FIG. 10 is a diagram schematically illustrating an example of the representative point angle ag according to the second embodiment. As illustrated in FIG. 10, a case in which a representative point P serving as a reference among representative points P included in a captured image CI is a representative point P1 will be described. The angle acquiring unit 120, for the representative point P1 and other representative points P (representative points P2 to P7) present in a target range ARd from the representative point P1 to a distance represented by a calculated distance CD, acquires an angle formed by segments respectively joining the representative point P1 and other representative points P adjacent to each other around a vertical axis having the representative point P1 as its center.

The angle acquiring unit 120 acquires an angle (a representative point angle ag1 illustrated in the drawing) formed by a segment joining the representative point P1 and the representative point P2 and a segment joining the representative point P1 and the representative point P3, acquires an angle (a representative point angle ag2 illustrated in the drawing) formed by a segment joining the representative point P1 and the representative point P3 and a segment joining the representative point P1 and the representative point P4, acquires an angle (a representative point angle ag3 illustrated in the drawing) formed by a segment joining the representative point P1 and the representative point P4 and a segment joining the representative point P1 and the representative point P5, acquires an angle (a representative point angle ag4 illustrated in the drawing) formed by a segment joining the representative point P1 and the representative point P5 and a segment joining the representative point P1 and the representative point P6, acquires an angle (a representative point angle ag5 illustrated in the drawing) formed by a segment joining the representative point P1 and the representative point P6 and a segment joining the representative point P1 and the representative point P7, and acquires an angle (a representative point angle ag6 illustrated in the drawing) formed by a segment joining the representative point P1 and the representative point P7 and a segment joining the representative point P1 and the representative point P2. The angle acquiring unit 120, for example, performs a similar process with one of all the representative points P included in the captured image CI set as the representative point P1. Thus, the angle acquiring unit 120 acquires information representing the representative point angles ag1 to ag6 with each of representative points P of cells imaged in a captured image CI set as the representative point P for each representative point P and supplies the acquired information to the cell distribution information acquiring unit 114.

For the representative points P2 to P7 of other target objects present in a target range ARd having the representative point P1 of a certain cell among a plurality of cells as its center, an angle (in other words, a representative point angle ag) formed by segments joining the representative point P1 and other representative points P2 to P7 adjacent to each other around a vertical axis having the representative point P1 as its center is an example of "characteristics of a target object".

The cell distribution information acquiring unit 114 acquires the representative point angle ag acquired by the angle acquiring unit 120. The cell distribution information acquiring unit 114 generates cell distribution information DI2 on the basis of the representative point angle ag and the determination angle DA. The determination angle DA is a representative point angle ag in a case in which cells are determined to be appropriately mature. The cell distribution information DI2 is information in which the number of representative point angles ag coinciding with the determination angle DA among the representative point angles ag1 to ag6 or the number of representative point angles ag of the determination angle DA±5 degrees and the frequency are associated with each other. The process of the cell distribution information acquiring unit 114 generating the cell distribution information DI2 is similar to the process of the cell distribution information acquiring unit 114 generating the cell distribution information DI1, and thus description thereof will be omitted.

As described above, in a case in which cells are assumed to be appropriately mature, cells adjacent to each other are arranged in a honeycomb shape. In a case in which cells (representative points P) are arranged in a honeycomb shape, the determination angle DA that may be taken is 60 degrees. Thus, in a case in which the representative point angle ag coincides with the determination angle DA or is approximately the determination angle DA, the cells are determined to be appropriately mature.

The condition determination unit 116 determines that the cells are mature in a case in which the number represented by the number information NI1 (in other words, six) coincides with the number having the highest frequency represented by the cell distribution information DI2 and determines that the cells are immature in a case in which the number represented by the number information NI1 does not coincide with the number having the highest frequency represented by the cell distribution information DI2.

<Process Flow>

Figure 11:
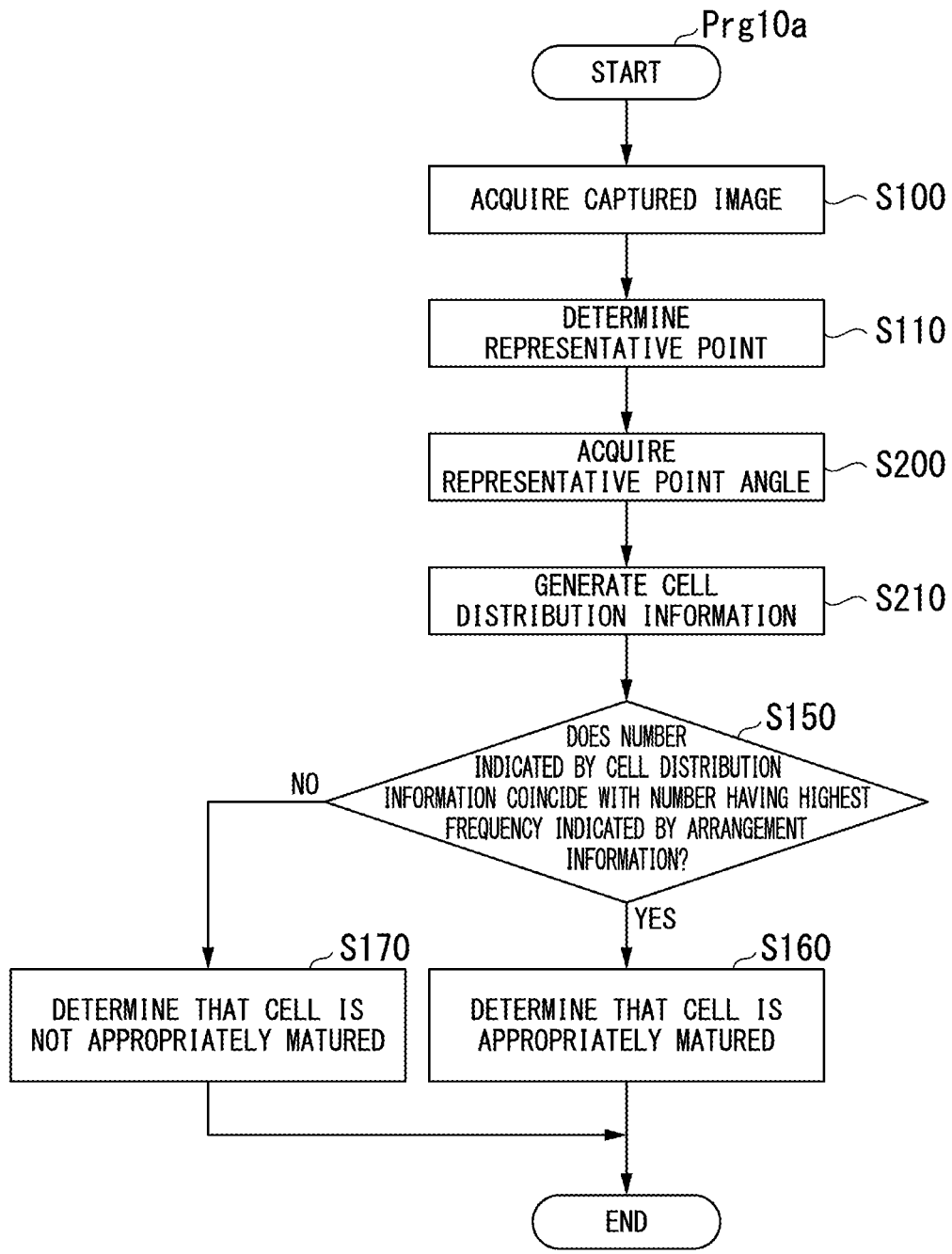
FIG. 11 is a flowchart illustrating an example of the operation of a determination device 10a according to the second embodiment.

Next, an operation of the determination device 10a determining a degree of maturity of cells will be described with reference to FIG. 11. FIG. 11 is a flowchart illustrating an example of the operation of the determination device 10a according to the second embodiment. The determination device 10a executes Steps S100 to S210 illustrated in FIG. 11 on the basis of a determination program Prg10a that is a control program for determining whether or not cells are appropriately mature. Processes of Steps S100 to S170 illustrated in FIG. 11 are similar to the processes having the same step numbers in FIG. 8, and thus description thereof will be omitted.

The determination program Prg10a executes Step S200 instead of (or in addition to) Step S120 executed by the determination program Prg10 and executes Step S210 instead of (or in addition to) Step S130. More specifically, the angle acquiring unit 120 sets one certain representative point P included in a captured image CI as a reference and acquires a representative point angle ag that is an angle formed by segments respectively joining different representative points P, which are present in a range from the representative point P serving as the reference to a distance represented by the calculated distance CD, of two other target objects adjacent to each other around a vertical axis having the representative point P serving as the reference as its center and a certain representative point P (Step S200). The cell distribution information acquiring unit 114 generates cell distribution information DI2 on the basis of the representative point angle ag for each representative point P acquired by the angle acquiring unit 120 (Step S210).

Summary of Second Embodiment

As described above, in the determination system 2 according to this embodiment, cell distribution information DI2 is acquired on the basis of an angle (in this example, the representative point angle ag) formed by segments respectively joining representative points P of two other cells adjacent to each other around a vertical axis having a representative point P of a certain cell as its center in the captured image CI and the representative point P of the certain cell, it is determined whether or not conditions of the cells (in this example, the degree of maturity of the cells) is good, and the accuracy of the determination of the degree of maturity of the cells can be improved.

Third Embodiment

Next, a third embodiment of the present invention will be described. In the first embodiment and the second embodiment, a case in which it is determined whether or not cells are mature for cells present in the target range ARd having the representative point P1 of a certain cell as its center has been described. Hereinafter, in the third embodiment and a fourth embodiment, a case in which it is determined whether or not cells are mature on the basis of information relating to sizes of cells imaged in a captured image CI will be described. In the third embodiment, a case in which it is determined whether or not cells are mature on the basis of areas of cells imaged in a captured image CI will be described. The same reference signs will be assigned to the same components as those according to the embodiment described above, and description thereof will be omitted.

Figure 12:
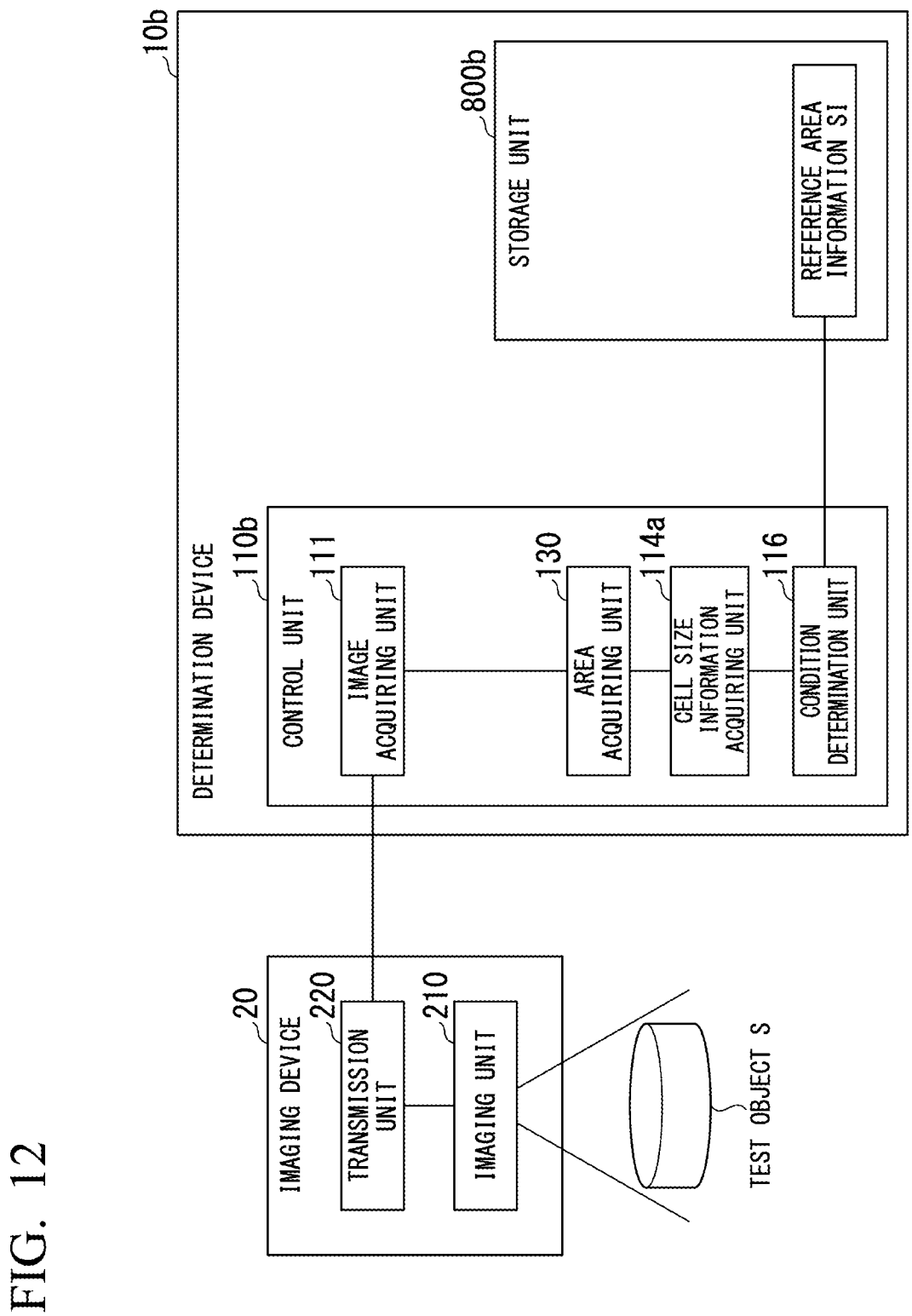
FIG. 12 is a diagram illustrating an example of the configuration of a determination system 3 according to a third embodiment.

FIG. 12 is a diagram illustrating an example of the configuration of a determination system 3 according to the third embodiment. The determination system 3 includes a determination device 10b and an imaging device 20.

The determination device 10b includes a control unit 110b and a storage unit 800b. Instead of (or in addition to) the information stored in the storage unit 800 and the storage unit 800a, reference area information SI is stored in the storage unit 800b in advance. Details of the reference area information SI will be described below. The control unit 110b, instead of (or in addition to) the components included in the control unit 110 or the control unit 110a, realizes an image acquiring unit 111, a cell size information acquiring unit 114a, a condition determination unit 116, and an area acquiring unit 130 as its functional units. The area acquiring unit 130 acquires an area of cells imaged in the captured image CI.

Figure 13:
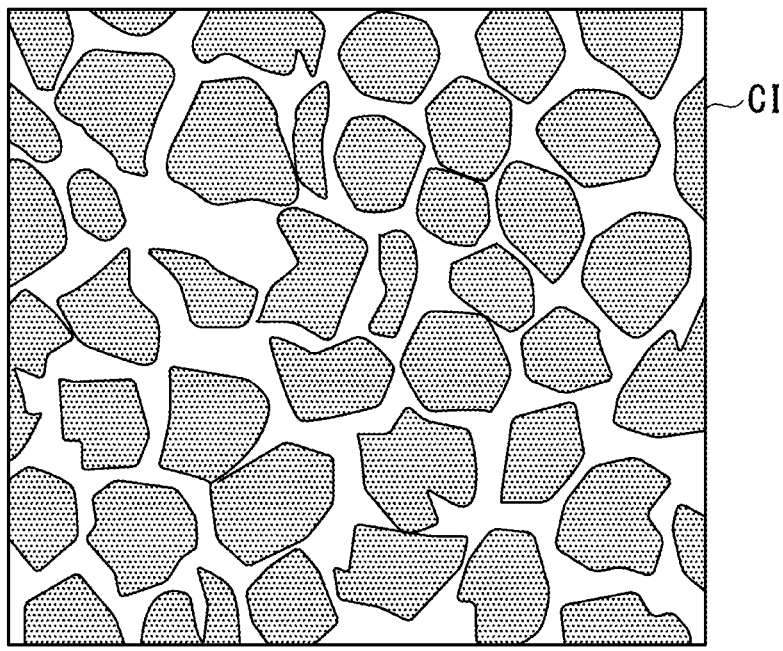
FIG. 13 is a diagram schematically illustrating the process of an area acquiring unit 130 according to the third embodiment.

FIG. 13 is a diagram schematically illustrating the process of the area acquiring unit 130 according to the third embodiment. For example, the area acquiring unit 130 identifies areas of a plurality of cells and areas of other than a cell imaged in a captured image CI by performing a smoothing process or a morphological filter process on the captured image CI. Next, the area acquiring unit 130 acquires areas of a plurality of cells for each cell on the basis of the areas of the plurality of cells that have been identified. Areas of a plurality of cells are an example of "characteristics of a target object".

Figure 14:
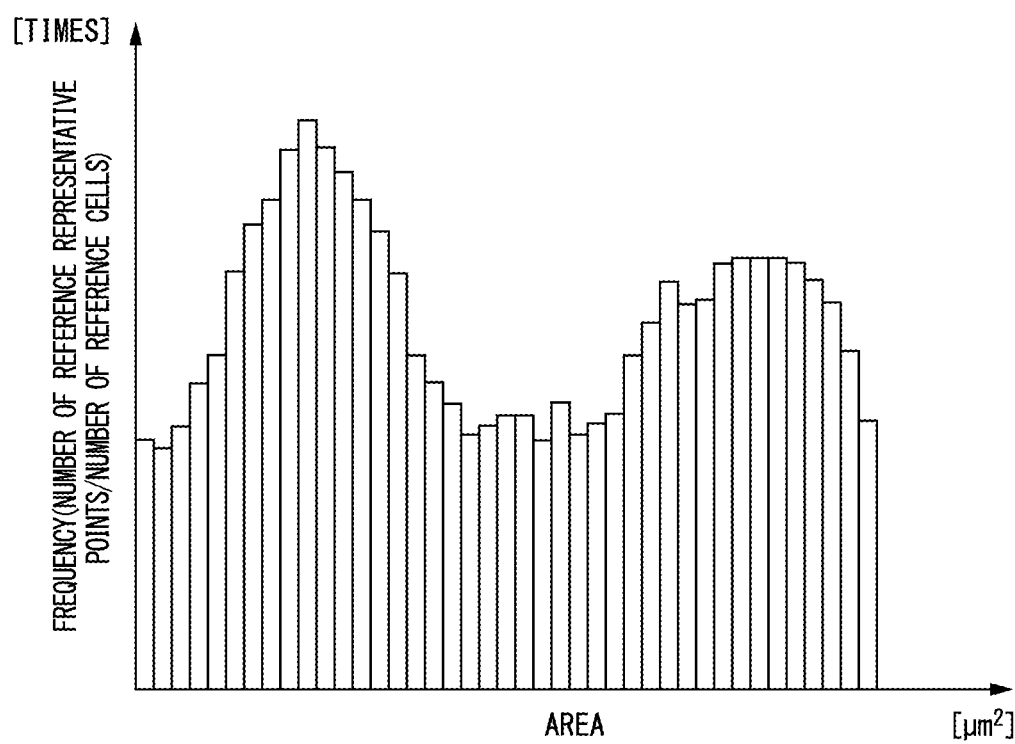
FIG. 14 is a diagram illustrating an example of cell size information DI3 according to the third embodiment.

FIG. 14 is a diagram illustrating an example of cell size information DI3 according to the third embodiment. The cell size information acquiring unit 114a generates cell size information DI3 on the basis of the areas of cells for each cell acquired by the area acquiring unit 130. The cell size information DI3 is information in which an area of a cell and the number (frequency) of cells in the area included in the captured image CI are associated with each other.

Referring back to FIG. 12, the condition determination unit 116 determines whether or not the degree of maturity of cells is good on the basis of the cell size information DI3 generated by the cell size information acquiring unit 114a and the reference area information SI. The reference area information SI is information that represents an area of a cell (hereinafter, referred to as a reference area) in a case in which cells are assumed to be appropriately mature.

Figure 15:
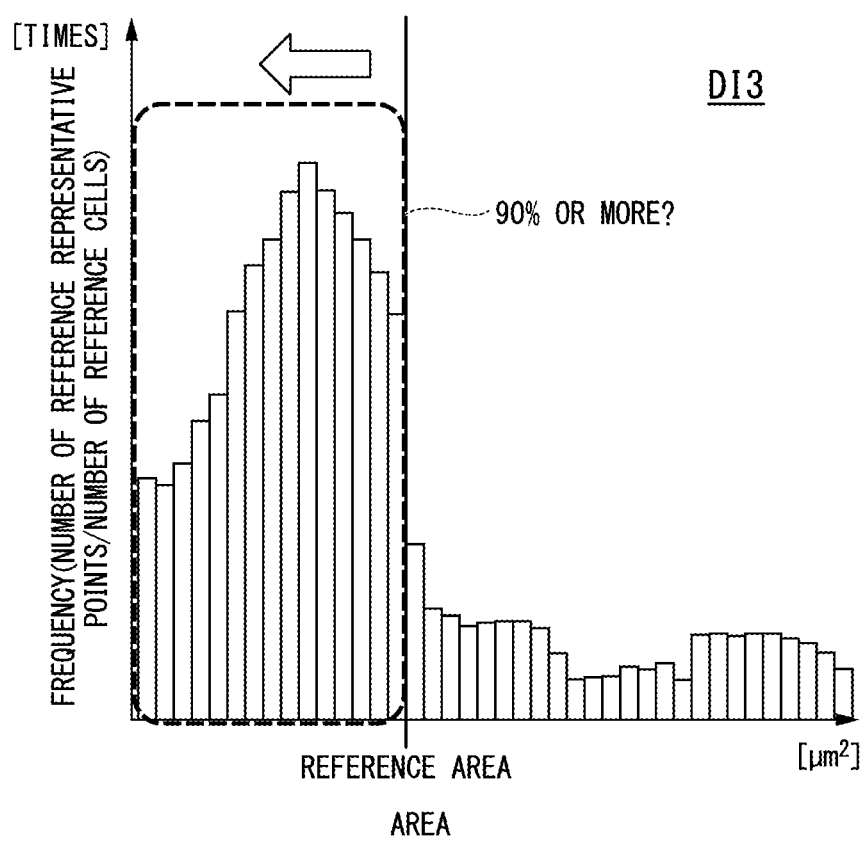
FIG. 15 is a diagram schematically illustrating an example of a determination process of a condition determination unit 116 according to the third embodiment.

FIG. 15 is a diagram schematically illustrating an example of a determination process of the condition determination unit 116 according to the third embodiment. For example, the condition determination unit 116 determines that cells are mature in a case in which a proportion occupied by (a frequency of) cells having an area smaller than the reference area represented by the reference area information SI among all the cells imaged in a captured image CI (in other words, a total number of frequencies represented by the cell size information DI3) is equal to or higher than a predetermined proportion (for example, 90% or more) and determines that the cells are immature in a case in which the proportion is less than the predetermined proportion.

<Process Flow>

Figure 16:
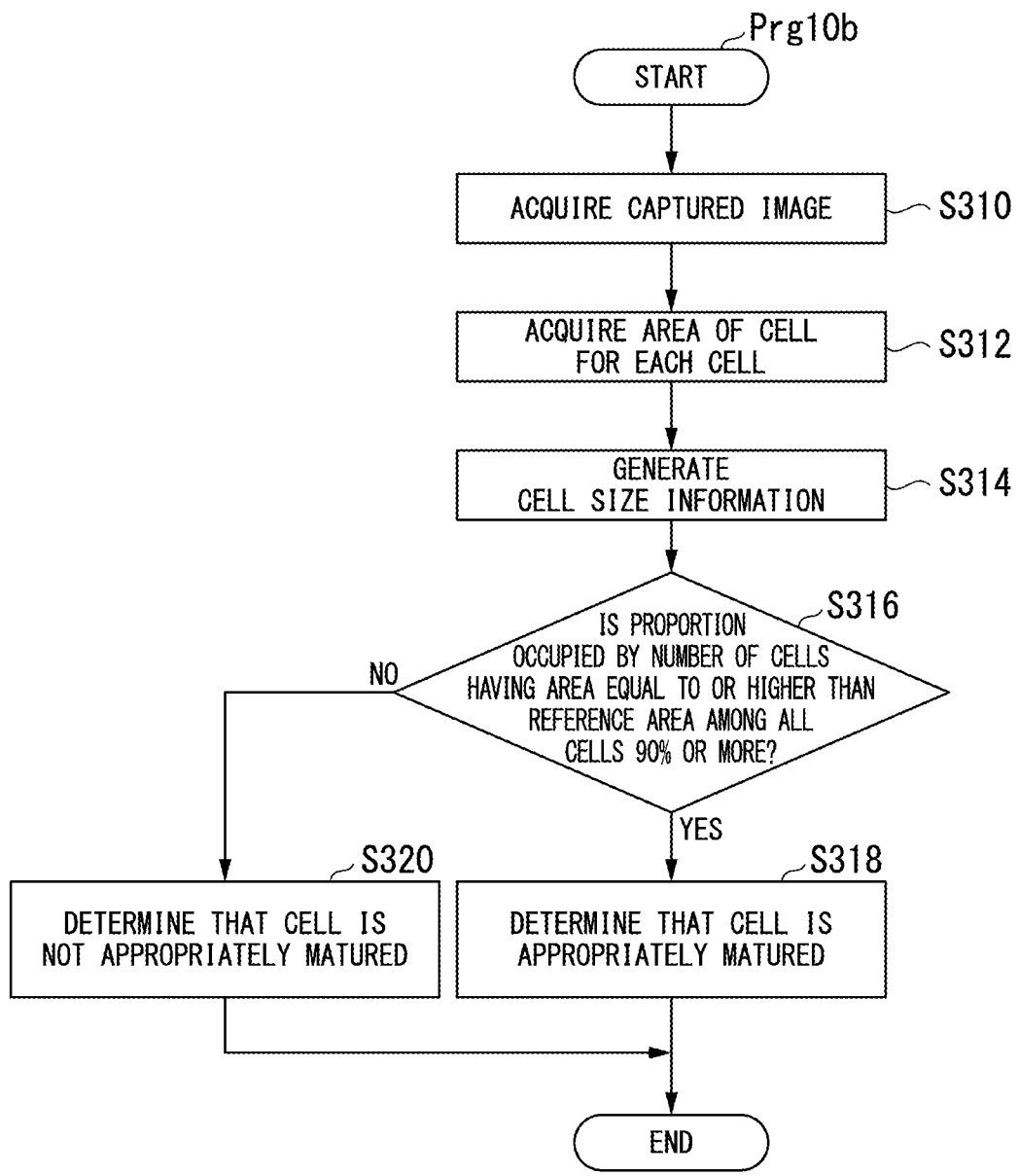
FIG. 16 is a flowchart illustrating an example of the operation of a determination device 10b according to the third embodiment.

Next, an operation of the determination device 10b determining a degree of maturity of cells will be described with reference to FIG. 16. FIG. 16 is a flowchart illustrating an example of the operation of the determination device 10b according to the third embodiment. The determination device 10b executes Steps S310 to S320 illustrated in FIG. 16 on the basis of a determination program Prg10b that is a control program for determining whether or not cells are appropriately mature.

The image acquiring unit 111 acquires a captured image CI from the imaging device 20 and supplies the acquired captured image to the representative point determining unit 112 (Step S310). The area acquiring unit 130 acquires areas of a plurality of cells imaged in the captured image CI for each cell on the basis of the captured image CI acquired by the image acquiring unit 111 (Step S312). The cell size information acquiring unit 114a generates cell size information DI3 on the basis of the areas of the cells acquired by the area acquiring unit 130 (Step S314).

The condition determination unit 116 determines whether or not a proportion occupied by cells having an area less than the reference area represented by the reference area information SI among all the cells imaged in the captured image CI is equal to or higher than a predetermined proportion (90% or more illustrated in the drawing) on the basis of the cell size information DI3 generated by the cell size information acquiring unit 114a (Step S316). The condition determination unit 116 determines that cells are mature in a case in which the proportion occupied by the number of cells having an area less than the reference area among all the cells imaged in the captured image CI is equal to or higher than a predetermined proportion (Step S316; Yes) (Step S318). The condition determination unit 116 determines that the cells are immature in a case in which the proportion occupied by the number of cells having an area less than the reference area among all the cells imaged in the captured image CI is less than the predetermined proportion (Step S316; No) (Step S320).

Summary of Third Embodiment

As described above, in the determination system 3 according to this embodiment, areas of a plurality of cells are included in the characteristics of a plurality of target objects (in this example, cells), and the condition determination unit 116 determines whether or not a condition of the cells is good on the basis of the areas of cells for each cell acquired by the characteristics acquiring unit (in this example, the area acquiring unit 130) and a predetermined area (in this example, the reference area information SI) and can improve the accuracy of determination of the degree maturity of the cells.

In the description presented above, although a case in which the condition determination unit 116 determines whether or not a degree of maturity of cells is good on the basis of the reference area information SI has been described, the determination is not limited thereto. The condition determination unit 116 may be configured to determine whether or not a degree of maturity of cells is good on the basis of reference average area information ASI instead of the reference area information SI. The reference average area information ASI is information that represents an average of areas of cells (hereinafter, a reference average area) in a case in which the cells are assumed to be appropriately mature.

Figure 17:
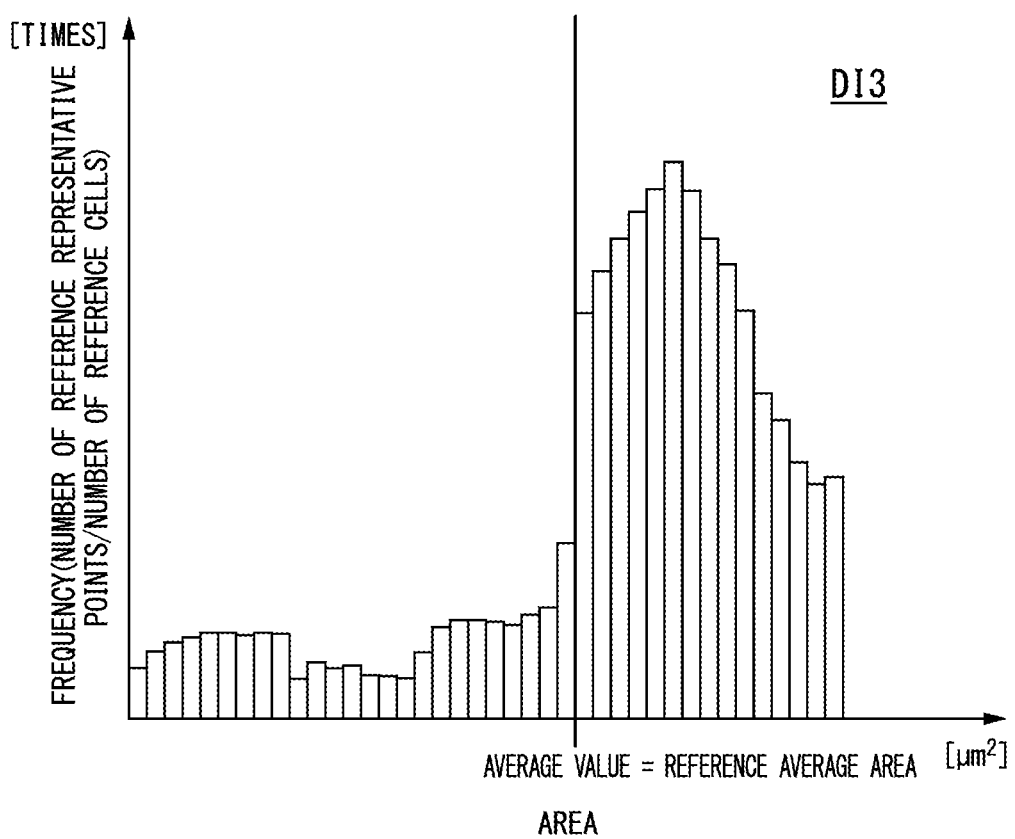
FIG. 17 is a diagram schematically illustrating another example of the determination process of a condition determination unit 16 according to the third embodiment.

FIG. 17 is a diagram schematically illustrating another example of the determination process of the condition determination unit 116 according to the third embodiment. For example, the condition determination unit 116 determines that cells are mature in a case in which an average of areas of all the cells imaged in the captured image CI matches the reference average area represented by the reference average area information ASI, coincides with the reference average area, or is less than the reference average area and determines that cells are immature in a case in which an average of areas of all the cells does not match the reference average area represented by the reference average area information ASI, does not coincide therewith, or is larger than the reference average area. The reference average area information ASI may be a median value of areas of cells instead of the average of the areas of the cells in a case in which the cells are assumed to be appropriately mature.

Fourth Embodiment

Next, a fourth embodiment of the present invention will be described. In the third embodiment, a case in which it is determined whether or not cells are mature on the basis of areas of cells imaged in a captured image CI has been described. In the fourth embodiment, the information relating to sizes of cells imaged in a captured image CI is replaced by areas, and determination is performed on the basis of the number of the cells. The same reference signs will be assigned to the same components as those according to the embodiment described above, and description thereof will be omitted.

Figure 18:
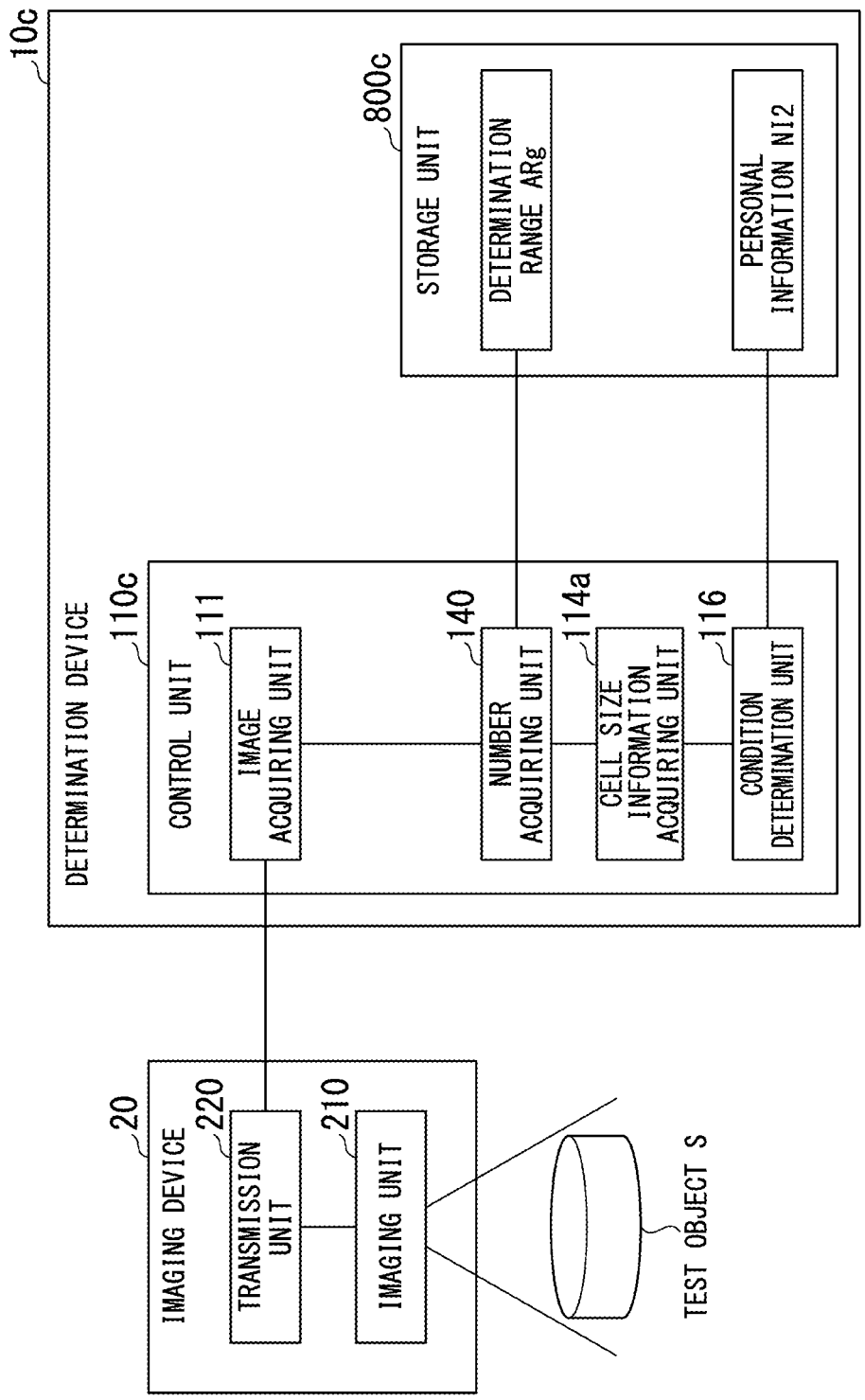
FIG. 18 is a diagram illustrating an example of the configuration of a determination system 4 according to a fourth embodiment.

FIG. 18 is a diagram illustrating an example of the configuration of a determination system 4 according to the fourth embodiment. The determination system 4 includes a determination device 10c and an imaging device 20.

The determination device 10c includes a control unit 110c and a storage unit 800c. Instead of (or in addition to) the information stored in the storage unit 800, the storage unit 800a, and the storage unit 800b, information representing the determination range ARg described above and number information NI2 are stored in the storage unit 800c in advance. The number information NI2 is information that represents the number of cells present in the determination range ARg (in other words, seven) in a case in which the cells are assumed to be appropriately mature. The control unit 110c, instead of (or in addition to) the components included in the control unit 110, the control unit 110a, or the control unit 110b, realizes an image acquiring unit 111, a cell size information acquiring unit 114a, a condition determination unit 116, and a number acquiring unit 140 as its functional units.

Figure 19:
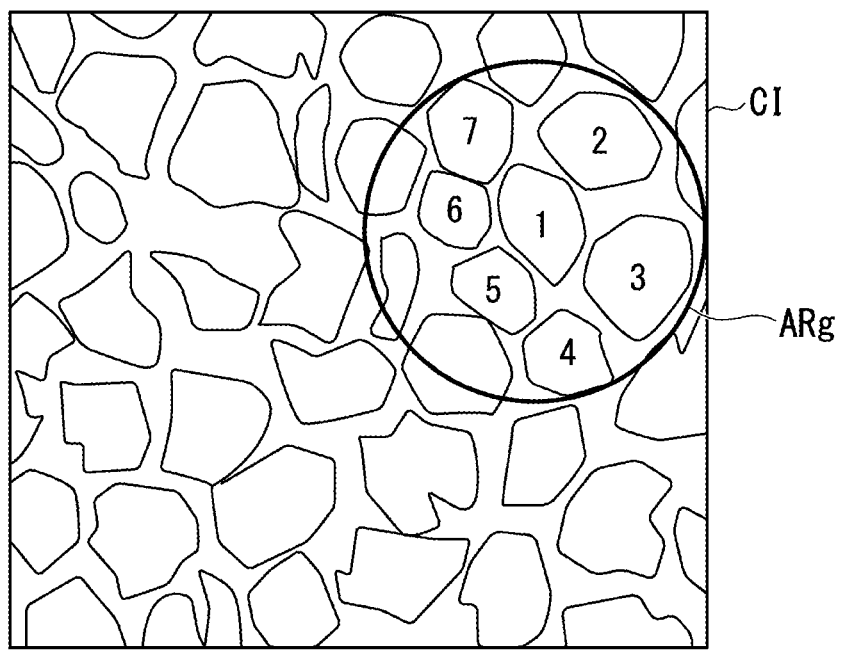
FIG. 19 is a diagram schematically illustrating the process of a number acquiring unit 140 according to the fourth embodiment.

FIG. 19 is a diagram schematically illustrating the process of the number acquiring unit 140 according to the fourth embodiment. For example, the number acquiring unit 140 identifies areas of a plurality of cells and areas of other than a cell imaged in a captured image CI by performing a smoothing process or a morphological filter process on the captured image CI. Next, the number acquiring unit 140 acquires the number of cells for each determination range ARg on the basis of the areas of the plurality of cells that have been identified. As illustrated in FIG. 19, the number acquiring unit 140 does not count up a cell of which part is present in the determination range ARg as a cell that is present in the determination range ARg. The shape of the determination range ARg may be a circle or any other shape. The number of cells present in the determination range ARg is an example of "characteristics of a target object".

The cell size information acquiring unit 114a generates cell size information DI4 on the basis of the number of cells present in the determination range ARg that has been acquired by the number acquiring unit 140. The cell size information DI4 is information in which the number of cells present in the determination range ARg and the frequency of the determination range ARg of the number are associated with each other.

The condition determination unit 116 determines whether or not cells are appropriately mature on the basis of the cell size information DI4 and the number information NI2. As described above, in a case in which the cells are assumed to be appropriately mature, the number of cells present in the determination range ARg (in other words, seven) is represented by the number information NI2. The condition determination unit 116 determines that cells are mature in a case in which the number represented by the number information NI2 coincides with the number of a highest frequency represented by the cell size information DI4 or in a case in which the number of a highest frequency represented by the cell size information DI4 is equal to or more than the number represented by the number information NI2 and determines that cells are immature in a case in which the number represented by the number information NI2 does not coincide with the number of a highest frequency represented by the cell size information DI4 or in a case in which the number of a highest frequency represented by the cell size information DI4 is less than the number represented by the number information NI2.

Summary of Fourth Embodiment

As described above, in the determination system 4 according to this embodiment, the number of cells present in a predetermined range (in this example, the determination range ARg) is included in characteristics of a plurality of target objects (in this example, cells), and the condition determination unit 116 determines whether or not a condition of the cells is good on the basis of the number acquired by the characteristics acquiring unit (in this example, the number acquiring unit 140) and a predetermined number (in this example, the number information NI2).

In the description presented above, although a case in which the number acquiring unit 140 acquires the number of cells on the basis of the determination range ARg, the acquisition is not limited thereto. The number acquiring unit 140 may acquire the number of cells on the basis of a predetermined range other than the determination range ARg. In such a case, this predetermined range is required to be a range that constantly represents a constant range regardless of an image angle of the captured image CI.

Modified Example 1: Change of Cell Over Time

Hereinafter, Modified Example 1 according to the embodiment described above will be described. In the embodiment described above, a case in which it is determined whether or not cells are appropriately mature on the basis of one certain captured image CI acquired by imaging a test object S has been described. In Modified Example 1, a case in which it is determined whether or not cells are mature on the basis of a plurality of captured images CI that are captured for a test object S over time will be described.

Figure 20:
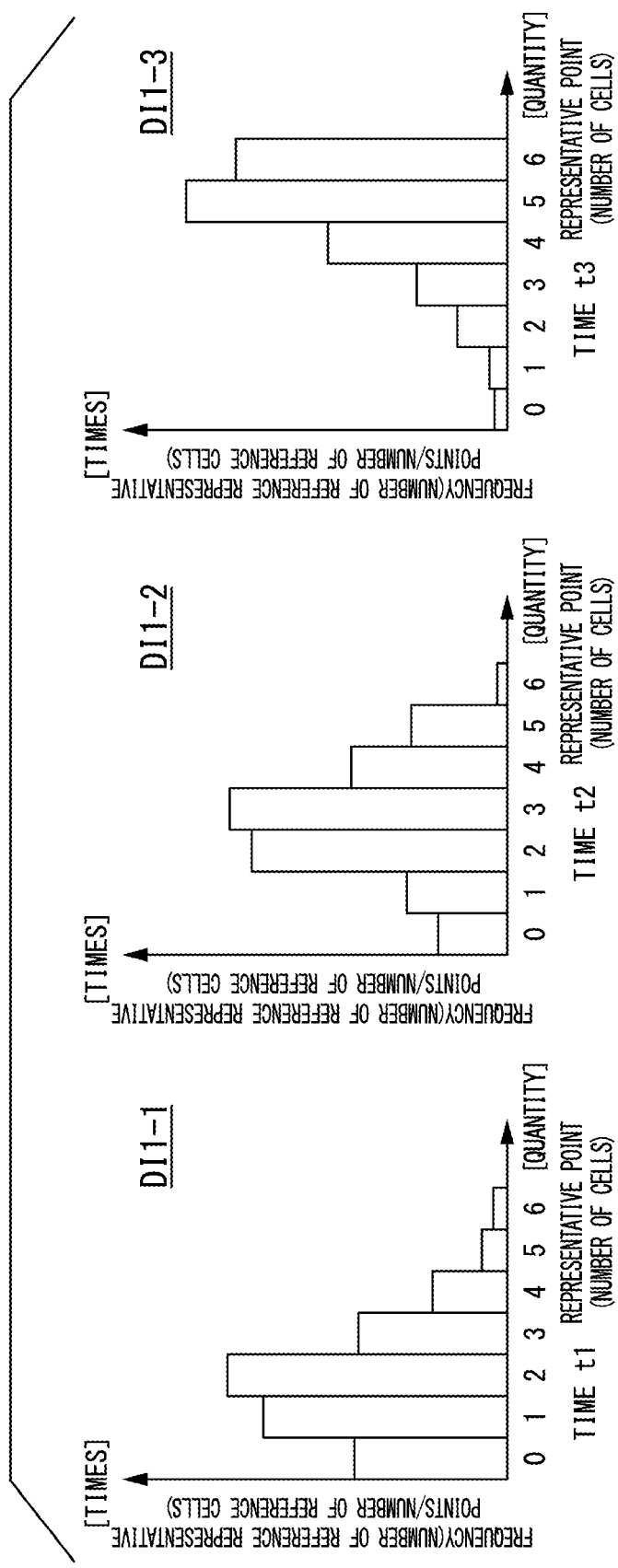
FIG. 20 is a diagram illustrating an example of changes of cell distribution information DI over time.

FIG. 20 is a diagram illustrating an example of changes of cell distribution information DI1 overtime. In this example, the imaging device 20, for example, images a test object S at a predetermined time interval and generates captured images CI. The determination device 10 generates cell distribution information DI1 on the basis of a plurality of captured images CI generated at a predetermined time interval and determines whether or not cells are mature. In one example illustrated in FIG. 20, cell distribution information DI1-1 is cell distribution information DI1 generated on the basis of a captured image CI captured at a certain time t1. Cell distribution information DI1-2 is cell distribution information DI1 generated on the basis of a captured image CI captured after a predetermined time has elapsed after the time t1. Cell distribution information DI1-3 is cell distribution information DI1 generated on the basis of a captured image CI captured after a predetermined time has elapsed after the time t2.

The condition determination unit 116, for example, compares trends in the frequency appearing in each piece of the cell distribution information DI1. In a case in which a frequency appearing in the cell distribution information DI1 has a predetermined trend, the condition determination unit 116 determines that cells are mature. The predetermined trend, for example, is a trend in which there is a high proportion of the number of other representative points P other than a representative point P1 within the determination range ARg being 0 to 2 at the time t1, there is a high proportion of the number of other representative points P other than the representative point P1 within the determination range ARg being 2 to 3 at the time t2, and there is a high proportion of the number of other representative points P other than the representative point P within the determination range ARg being 4 to 6 at the time t3. In a case in which a frequency represented by the cell distribution information DI1 represents such a trend, the condition determination unit 116 determines that the cells are mature. In a case in which a frequency represented by the cell distribution information DI1 does not represent such a trend, the condition determination unit 116 determines that the cells are not mature (in other words, the cells are immature).

The predetermined trend described above is one example and thus is not limited thereto. In the description presented above, although the cell distribution information DI1 has been described as one example, the condition determination unit 116 may similarly determine whether or not cells are mature on the basis of whether or not a trend of the frequency is a predetermined trend also for the other information (the cell distribution information DI2 or the cell size information DI3 and DI4).

Modified Example 2: Combination of Determination Criterion

Hereinafter, Modified Example 2 of the embodiment described above will be described. In the embodiment described, a case in which it is determined whether or not cells are mature on the basis of one certain captured image CI acquired by imaging a test object S has been described. In Modified Example 2, a case in which an index used for determining whether or not cells are mature is selected will be described.

Figure 21:
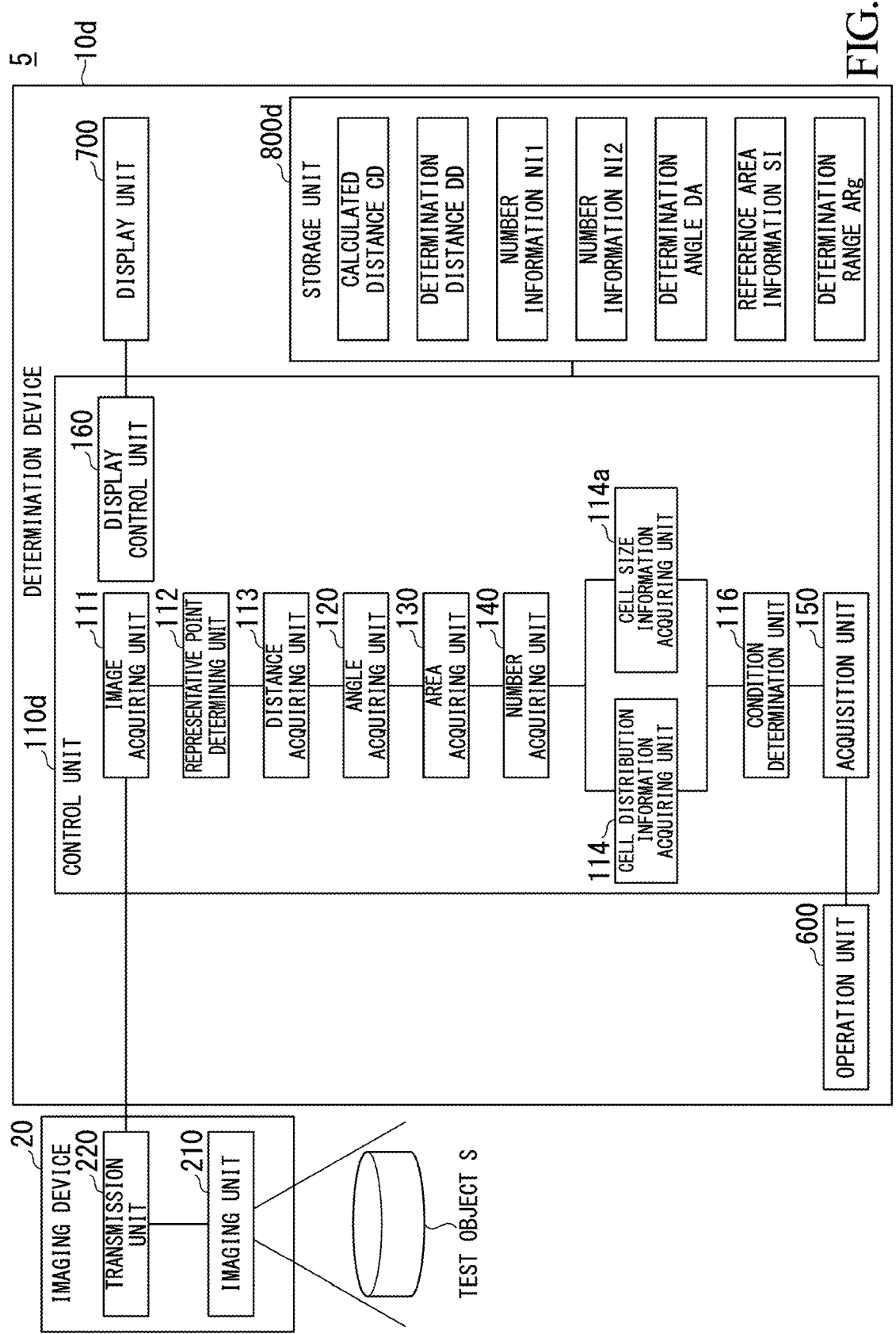
FIG. 21 is a diagram illustrating an example of the configuration of a determination system 5 according to Modified Example 2.

FIG. 21 is a diagram illustrating an example of the configuration of a determination system 5 according to Modified Example 2. The determination system 5 includes a determination device 10d and an imaging device 20.

The determination device 10d includes a control unit 110d, a storage unit 800d, an operation unit 600, and a display unit 700. The operation unit 600, for example, is an input device such as a keyboard, a touch pad, a mouse, or the like that accepts an operation input from a user. The display unit 700, for example, is a display device such as a liquid crystal display panel, a plasma display panel, an organic electroluminescence (EL) display panel, or the like.

The control unit 110d includes, among the functional units included in the control units 110 and 110a to 110c, an image acquiring unit 111, a cell distribution information acquiring unit 114, and a cell size information acquiring unit 114a, a functional unit corresponding to an index that may be selected (at least any one of a distance acquiring unit 113, a representative point determining unit 112, an angle acquiring unit 120, an area acquiring unit 130, and a number acquiring unit 140), a condition determination unit 116, an acquisition unit 150, and a display control unit 160. The display control unit 160 causes the operation unit 600 to display a graphical user interface (hereinafter referred to as a GUI) image stored in the storage unit 800d in advance.

Figure 22:
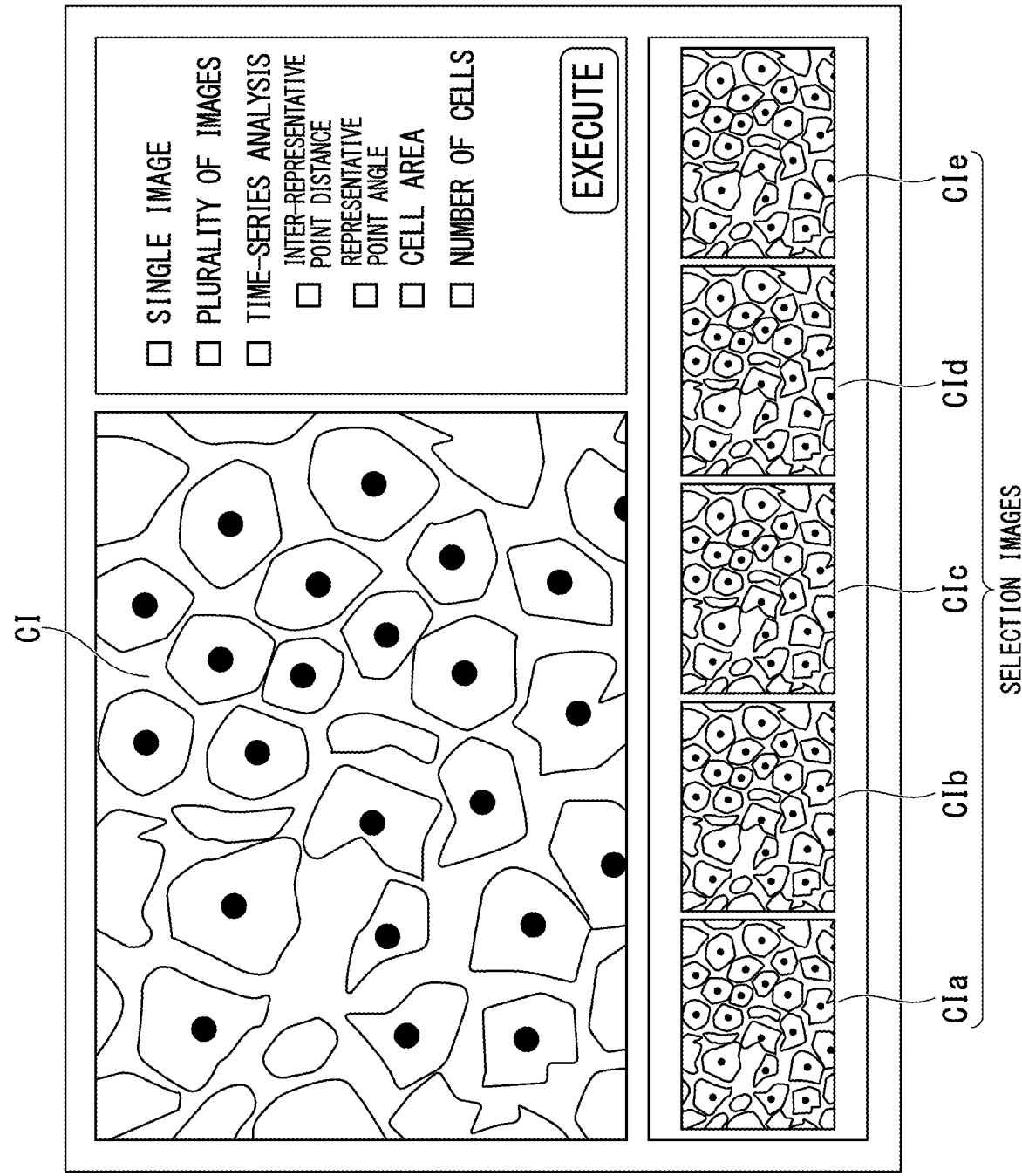
FIG. 22 is a diagram illustrating an example of a GUI image.

FIG. 22 is a diagram illustrating an example of a GUI image. The GUI image includes an area in which a list of a plurality of captured images CI (captured images CIa to CIe illustrated in the drawing) is displayed, an area in which a selection image is displayed, and an area in which a list of indexes is displayed. In the area in which the list of images is displayed, a captured image CI captured by the imaging device 20 in the past, captured images CI acquired by the imaging device 20 imaging a certain test object S at a predetermined time interval, and the like are included. Such captured images CI, for example, are stored in the storage unit 800d, and the display control unit 160 causes the display unit 700 to display the captured images CI stored in the storage unit 800d. The acquisition unit 150 acquires an operation accepted by the operation unit 600. The display control unit 160 displays a selected captured image CI in the area in which a selected image is displayed on the basis of "an operation selecting a captured image CI" acquired by the acquisition unit 150.

In the area in which the list of indexes is displayed, a check box used for selecting whether a captured image CI that is an analysis target is one image (in other words, a single image) or a plurality of images appears. In a case in which a single image is selected using this check box, the determination system 5 determines whether or not cells are mature on the basis of one certain captured image CI. In a case in which a plurality of images are selected using this check box, the determination system 5 determines whether or not cells are mature on the basis of the plurality of captured images CI.

In the area in which the list of indexes is displayed, a check box of "inter-representative point distance", "representative point angle", "cell area", and "the number of cells" representing options of indexes used when it is determined whether or not cells are mature on the basis of a single captured image or a plurality of captured images CI appears. The determination system 5 analyzes the captured image CI in accordance with an index selected using this check box and determines whether or not cells are mature. In addition, the determination system 5 outputs a histogram (for example, cell distribution information DI1 and DI2 and cell size information DI3 and DI4). Such indexes are examples, and thus, the indexes are not limited thereto, and at least any one of "inter-representative point distance", "representative point angle", "cell area", and "the number of cells" may be configured to appear as a check box.

In addition, in the area in which the list of indexes is displayed, a check box of "time-series analysis" appears. In a case in which the check box of "time-series analysis" is checked, the determination system 5 determines whether or not cells are mature on the basis of time-series images. In addition, the determination system 5 outputs a result of the time-series analysis of the captured image CI.

Figure 23:
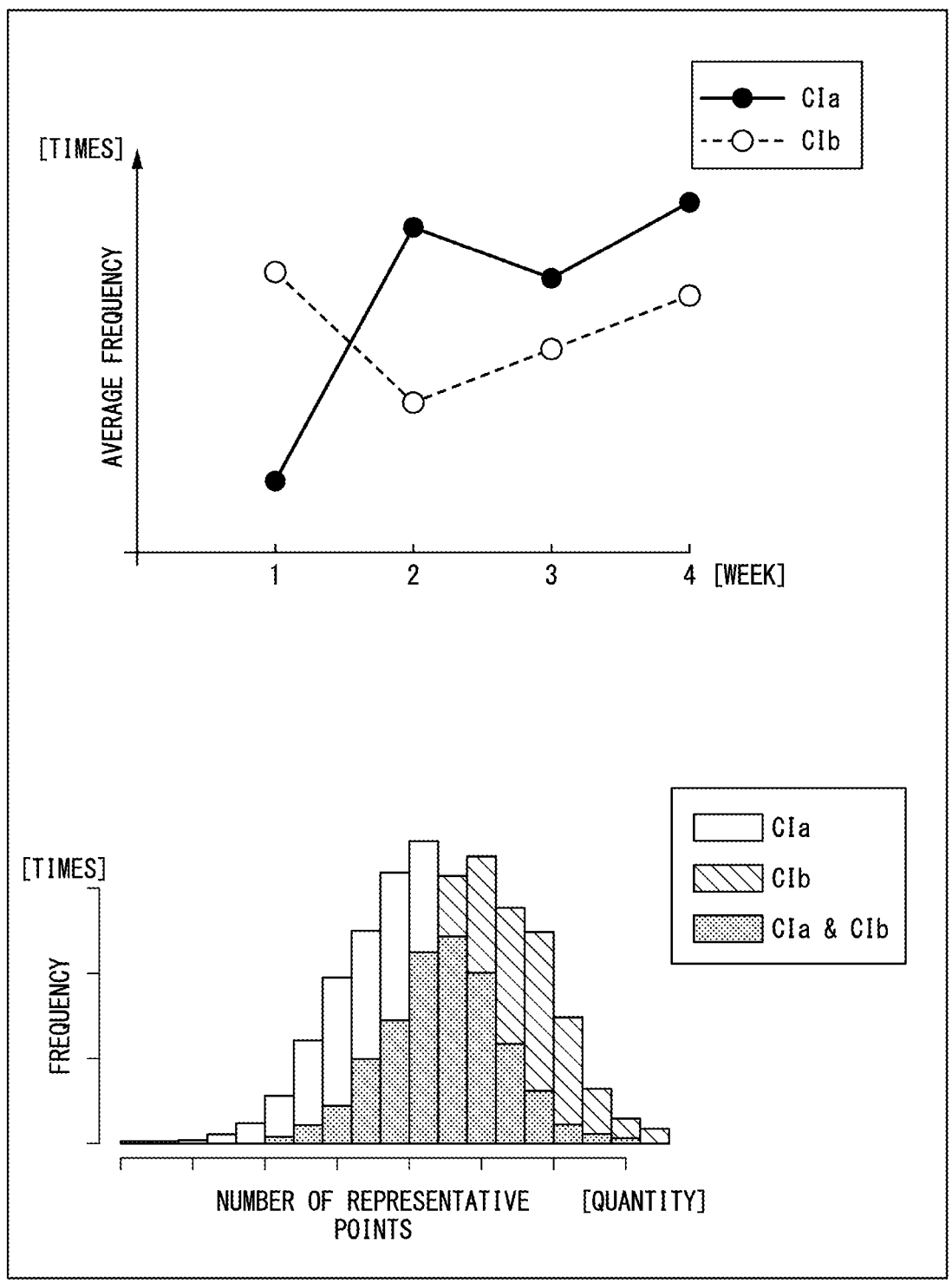
FIG. 23 is a diagram illustrating an example of a result image of a process executed by a GUI illustrated in FIG. 22.

FIG. 23 is a diagram illustrating an example of a result image of a process executed by the GUI illustrated in FIG. 22. More specifically, FIG. 23 is a diagram illustrating an example of a result image in a case in which "captured image CIa", "captured image CIb", "a plurality of images", "time-series analysis", and "inter-representative point distance" are selected using the GUI illustrated in FIG. 22. In the result image, for example, a graph in which an average frequency (or a highest frequency) of cell distribution information DI generated on the basis of the inter-representative point distance d at a certain timing (first to fourth weeks illustrated in the drawing) and the timing are associated with each other for each timing appears. In addition, in the result image, for example, an image in which an image representing cell distribution information DI (histogram) at a predetermined timing is represented in an overlapping manner is included.

In a case in which a plurality of check boxes among check boxes of "inter-representative point distance", "representative point angle", "cell area", and "the number of cells" are selected, the determination system 5 determines whether or not cells are mature on the basis of indexes selected using the plurality of check boxes and generates a result image illustrated in FIG. 23 for each of the results. In this case, in a case in which it is determined that cells are mature on the basis of at least one index among the plurality of indexes that have been selected, the determination system 5 determines that the cells are mature. In addition, in a case in which determination results based on all the indexes among the plurality of indexes indicate that cells are mature, the determination system 5 determines that the cells are mature.

In addition, the acquisition unit 150 acquires an operation of designating display of "a plurality of images" "time-series analysis", and "inter-representative point distance" appearing in the area in which the list of indexes is displayed using the operation unit 600. The control unit 110d acquires characteristics of cells imaged in the captured image CI on the basis of the index appearing in accordance with an operation acquired by the acquisition unit 150 and determines whether or not the cells are mature.

Here, although a case in which a target object imaged by the imaging device 20 is a test object S has been described, the target object is not limited thereto. A target object imaged by the imaging device 20 is a densely packed object, and the state of packing may be determined. For example, the target object may be a material having a hexagonal close-packed structure or may have a honeycomb structure.

Here, although a case in which part of a test object S is imaged by the imaging unit 210 has been described, the imaging is not limited thereto. The imaging unit 210 may image the entire test object S. In addition, here, although a case in which a plurality of cells are included in a captured image CI that is captured by the imaging unit 210 has been described, the configuration is not limited thereto. Only one cell may be included in a captured image CI that is captured by the imaging unit 210.

In addition, here, although a case in which the representative point determining unit 112 analyzes the captured image CI through a peak detection process has been described, the analysis is not limited thereto. The representative point determining unit 112 may analyze the captured image CI through a contrast process or through noise elimination. In addition, here, although a case in which a representative point P is a center of a cell included in the captured image CI has been described, the representative point is not limited thereto. The representative point P may be a point that represents a nucleus of a cell included in the captured image CI.

As above, although forms for performing the present invention have been described using several embodiments and modified examples, the present invention is not limited to such embodiments at all, and various modifications and substitutions can be made within a range not departing from the concept of the present invention.

What is claimed is:

1. An image analysis device comprising:
   a processor;
   a memory encoded with instructions executed by the processor, the instructions causing the processor to perform operations comprising:
   executing a distribution information acquiring unit to acquire, based on an image in which a plurality of cultivated cells are imaged, distribution information relating to a distribution in a predetermined range of the plurality of cultivated cells, wherein the distribution information relates to i) a number of representative points of other cells present in the predetermined range of which a center is a representative point of a predetermined cell among the plurality of cultivated cells, and ii) a frequency at which cells having the number of representative points are detected; and
   executing a determination unit to determine a cultivated state of the plurality of cultivated cells based on a number of the frequency indicated by the distribution information and the number of representative points of the other cells existing in the predetermined range.

2. The device according to claim 1, wherein at least one of a state of differentiation and a maturation state of cells is included in the cultivated state.

3. The device according to claim 1, wherein information relating to a relative positional relation of the plurality of cultivated cells on a medium is included in the distribution information.

4. The device according to claim 1, wherein the distribution information is acquired based on an inter-representative point distance between the representative point of the predetermined cell among the plurality of cultivated cells and the representative points of the other cells, and a determination distance that corresponds to the predetermined range.

5. The device according to claim 1, wherein the determination unit determines whether or not plurality of cultivated cells are mature based on a number having the highest frequency represented by the distribution information.

6. The device according to claim 1, wherein the distribution information is acquired based on an angle formed by segments respectively joining representative points of two other cells that are adjacent to each other around a vertical axis having a representative point of the predetermined cell as a center, and a determination angle that corresponds to the predetermined range.

7. The device according to claim 6,
wherein the determination unit determines whether or not the plurality of cultivated cells are mature based on a number having the highest frequency represented by the distribution information.

8. The device according to claim 1, further comprising:
executing a size information acquiring unit to acquire information relating to sizes of the plurality of cultivated cells,
wherein the determination unit determines a maturation state of the plurality of cultivated cells based on the information relating to the sizes of the cells.

9. The device according to claim 1, further comprising:
executing an acceptance unit to accept a user's operation; and
executing a display control unit to control display of a display,
wherein the distribution information acquiring unit acquires the distribution information designated by the user's operation accepted by the acceptance unit, and
wherein the display control unit causes the display to display at least one of an image used when the distribution information is acquired and an image indicating a determination result of the determination unit.

10. A system comprising:
the device according to claim 1; and
an imaging device configured to generate the image by imaging the plurality of cultivated cells.

11. A non-transitory storage medium storing a program that is executable by a computer to execute:
a distribution information acquiring step of acquiring, based on an image in which a plurality of cultivated cells that are cultivated in a predetermined area are imaged, distribution information relating to a distribution in the predetermined area of the plurality of cultivated cells, wherein the distribution information relates to i) a number of representative points of other cells present in the predetermined range of which a center is a representative point of a certain cell among the plurality of cultivated cells, and ii) a frequency at which cells having the number of representative points are detected; and
a determination step of determining a cultivated state of the plurality of cultivated cells based on a number of the frequency indicated by the distribution information and the number of representative points of the other cells existing in the predetermined range.

* * * * *